(12) United States Patent
Nakamura et al.

(10) Patent No.: US 8,133,912 B2
(45) Date of Patent: Mar. 13, 2012

(54) METHYL AQUOCOBYRINIC ACID DERIVATIVE, ALKYLATION COMPOSITION, AND METHOD FOR DETOXIFYING A HARMFUL COMPOUND BY UTILIZING THE COMPOSITION

(75) Inventors: Koichiro Nakamura, Tokyo (JP); Yoshio Hisaeda, Fukuoka (JP); Ling Pan, Fukuoka (JP)

(73) Assignees: Nippon Sheet Glass Company, Limited, Tokyo (JP); Kyushu University, Fukaoka (JP)

( * ) Notice: Subject to any disclaimer, the term of this patent is extended or adjusted under 35 U.S.C. 154(b) by 318 days.

(21) Appl. No.: 12/309,511

(22) PCT Filed: Jul. 24, 2007

(86) PCT No.: PCT/JP2007/000792
§ 371 (c)(1),
(2), (4) Date: Mar. 10, 2009

(87) PCT Pub. No.: WO2008/012948
PCT Pub. Date: Jan. 31, 2008

(65) Prior Publication Data
US 2009/0306362 A1  Dec. 10, 2009

(30) Foreign Application Priority Data

Jul. 26, 2006 (JP) ................. 2006-203732
Dec. 27, 2006 (JP) ................. 2006-350926
Mar. 1, 2007 (WO) ............. PCT/JP2007/000152
Jun. 20, 2007 (JP) ................. 2007-162028

(51) Int. Cl.
*A61K 31/409* (2006.01)
(52) U.S. Cl. ........................................ 514/410
(58) Field of Classification Search ........... 514/410
See application file for complete search history.

(56) References Cited

FOREIGN PATENT DOCUMENTS

| | | |
|---|---|---|
| JP | 3-504450 | 10/1991 |
| JP | 2006-191947 | 7/2006 |
| WO | 89/10772 | 11/1989 |
| WO | 2005/100268 | 10/2005 |
| WO | 2006/054757 | 5/2006 |

OTHER PUBLICATIONS

Kaise, et al., "Cytotoxicological Aspects of Organic Arsenic Compounds Contained in Marine Products Using the Mammalian Cell Culture Technique", Applied Organometallic Chemistry, vol. 12, 137-143 (1998).
Shimakoshi, et al., "Hydrophobic Vitamin $B_{12}$ Part 20:# Supernucleophilicity of Co(I) Heptamethyl Cobyrinate toward Various Organic Halides", Bull. Chem. Soc. Jpn., 78(5), 859-863 (2005).
Kräutler", et al., "Complementary Diastereoselective Cobalt Methylations of the Vitamin-$B_{12}$ Derivative Cobester", Helvetica Chimica Acta—vol. 67(7), 1891-1896 (1984).

*Primary Examiner* — James O Wilson
*Assistant Examiner* — Brian McDowell
(74) *Attorney, Agent, or Firm* — Hamre, Schumann, Mueller & Larson, P.C.

(57) ABSTRACT

The composition for the alkylation according to the present disclosure is characterized in that the composition contains the following cobalt complex. The method of detoxifying the harmful compound according to the present disclosure is characterized in that a harmful compound containing at least one element selected from the groups comprising arsenic, antimony and selenium is detoxified by the alkylation of the harmful compound, in the presence of the composition according to the present disclosure.

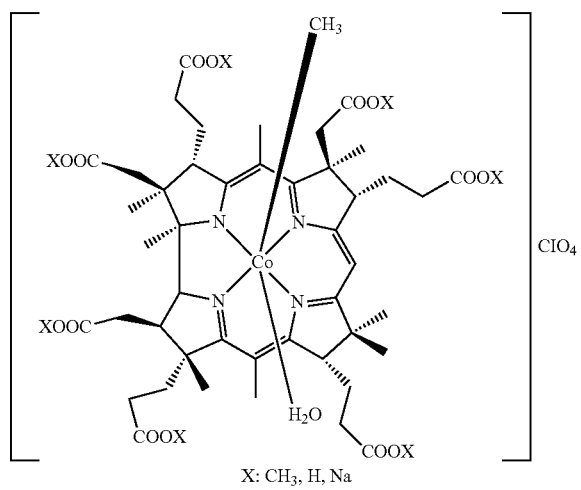

X: $CH_3$, H, Na

3 Claims, 15 Drawing Sheets

[Figure 1]
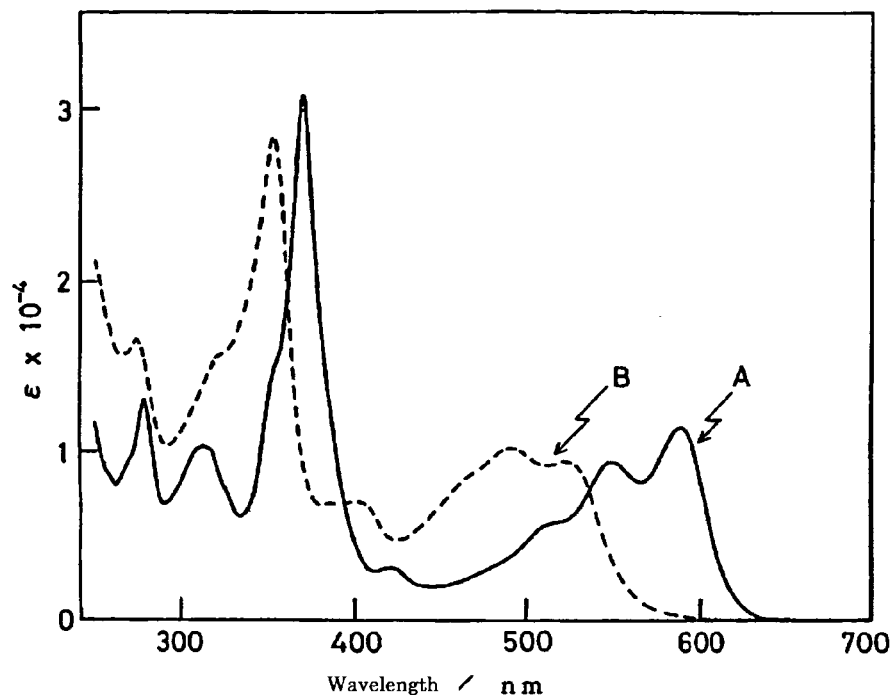
[Figure 2]
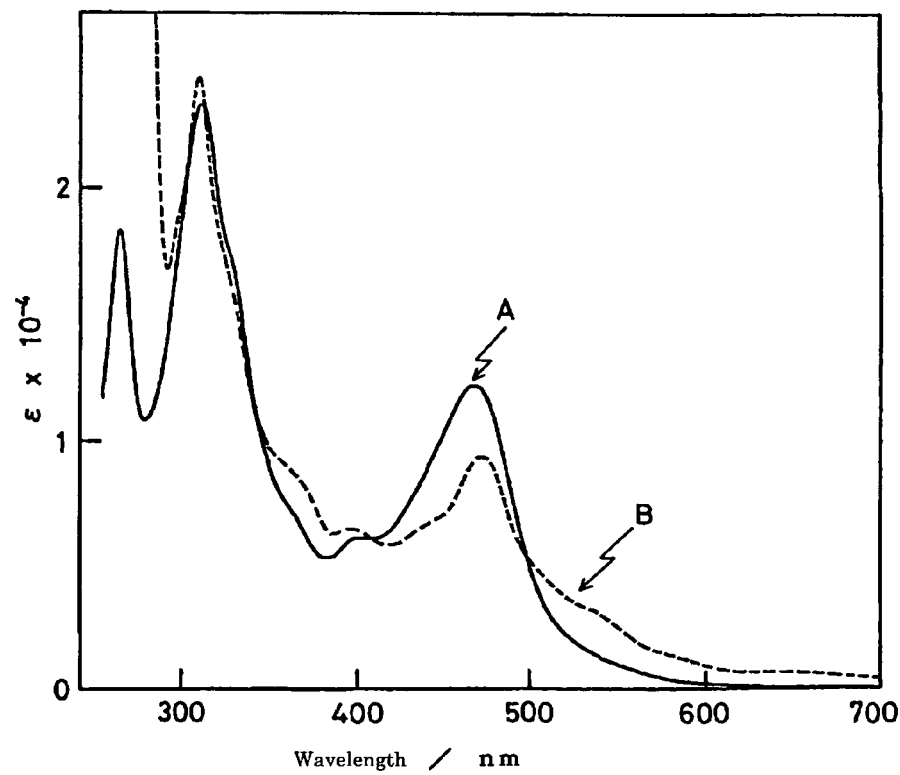

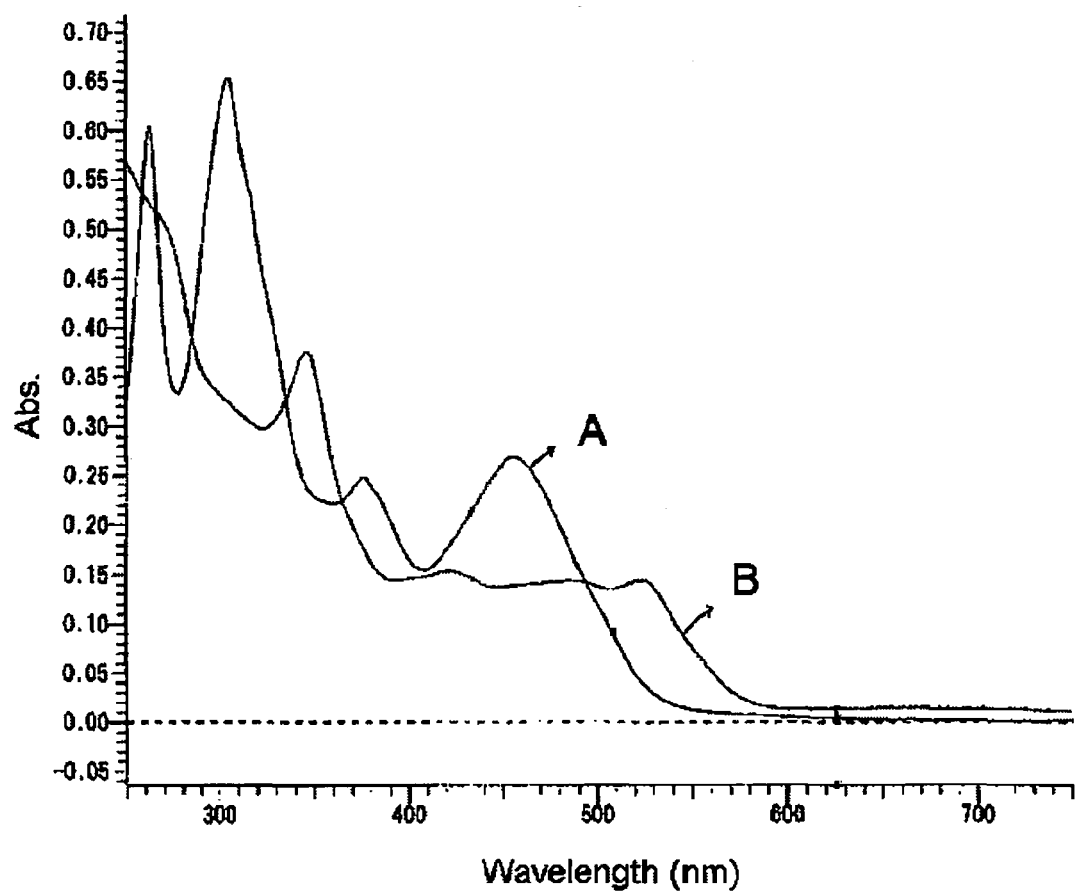
[Figure 3]

[Figure 4]
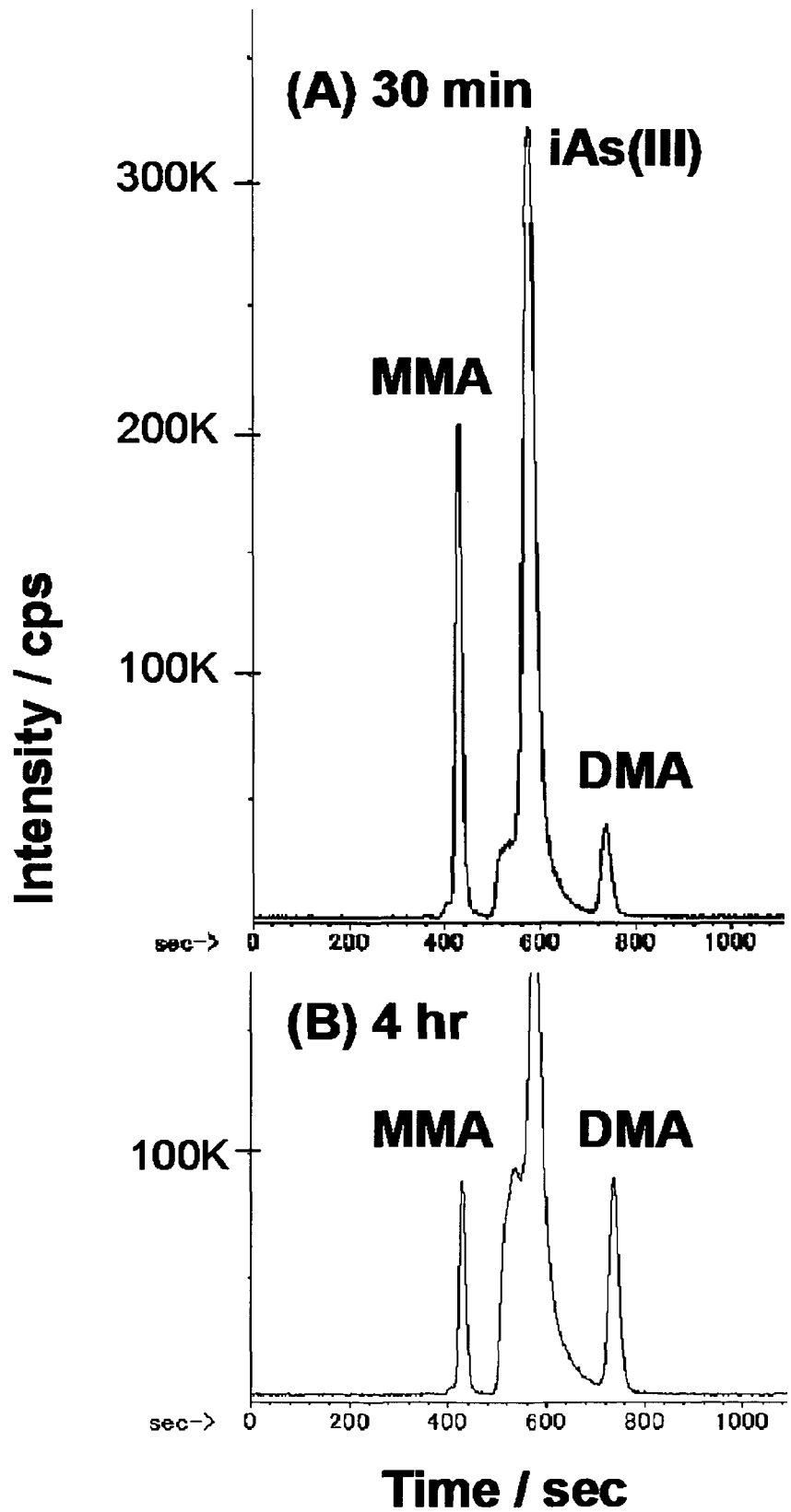

[Figure 5]
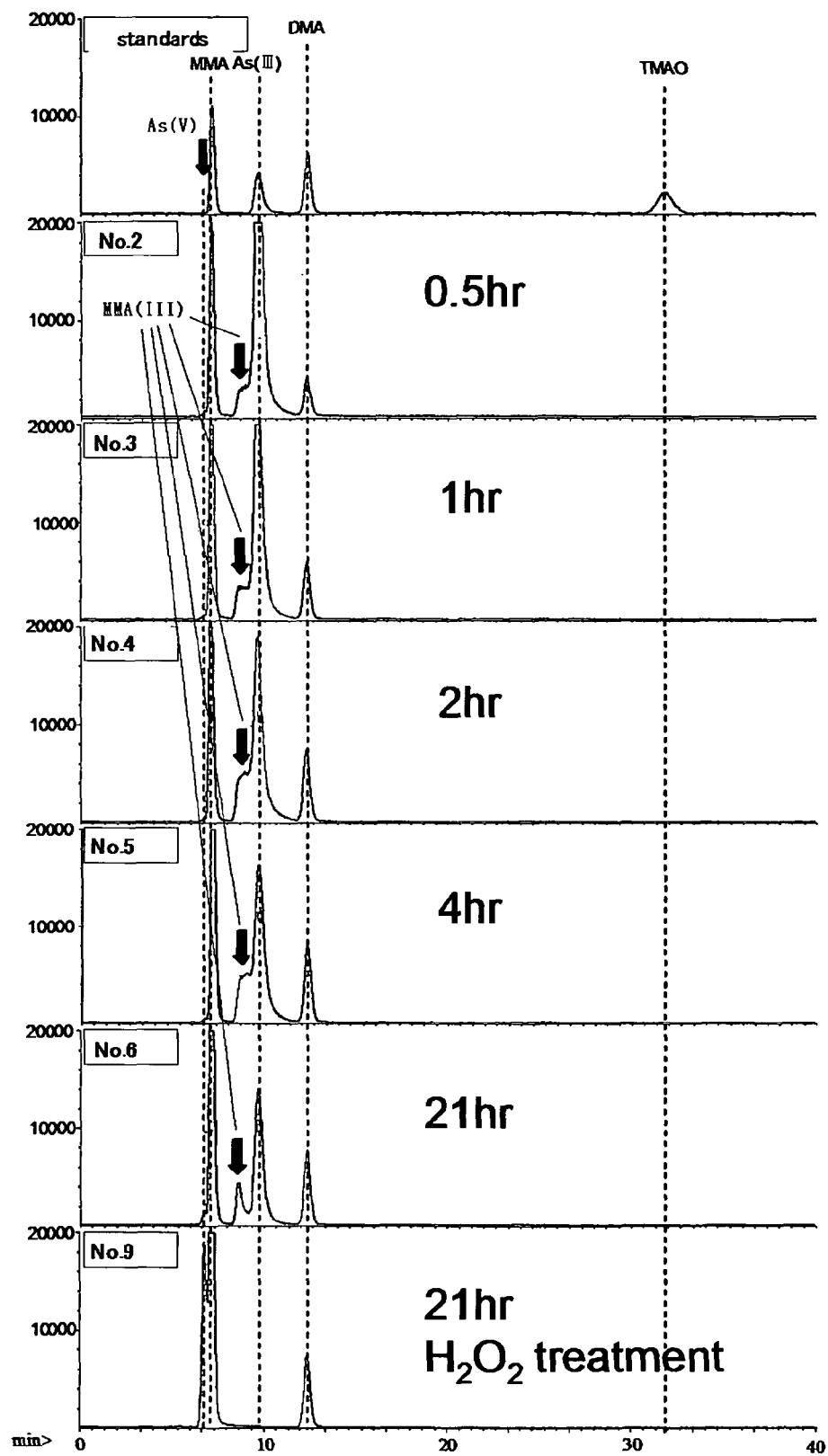

[Figure 6]
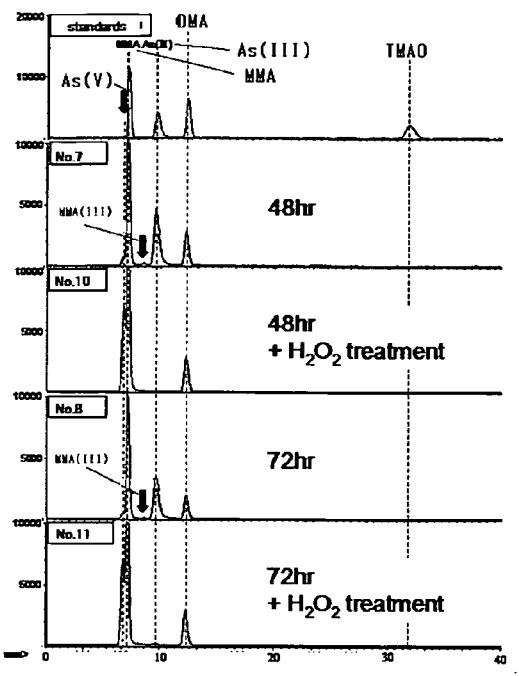
[Figure 7]
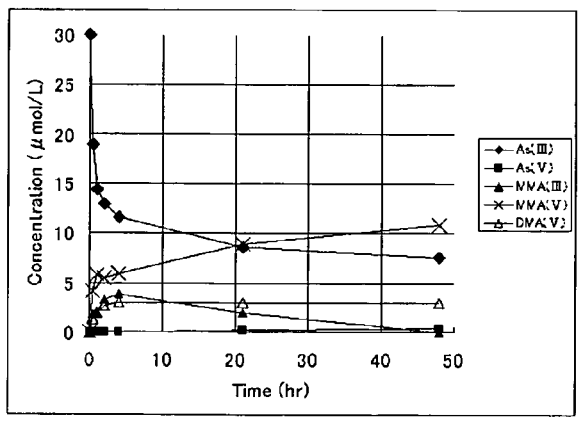
[Figure 8]
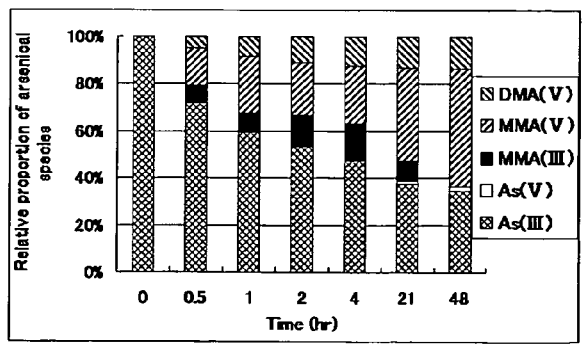

[Figure 9]
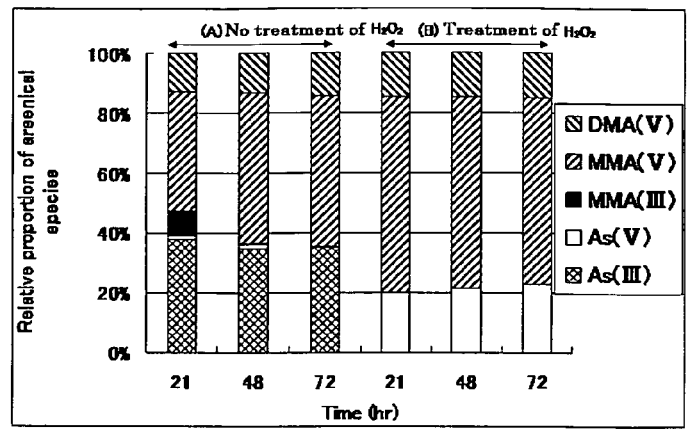
[Figure 10]
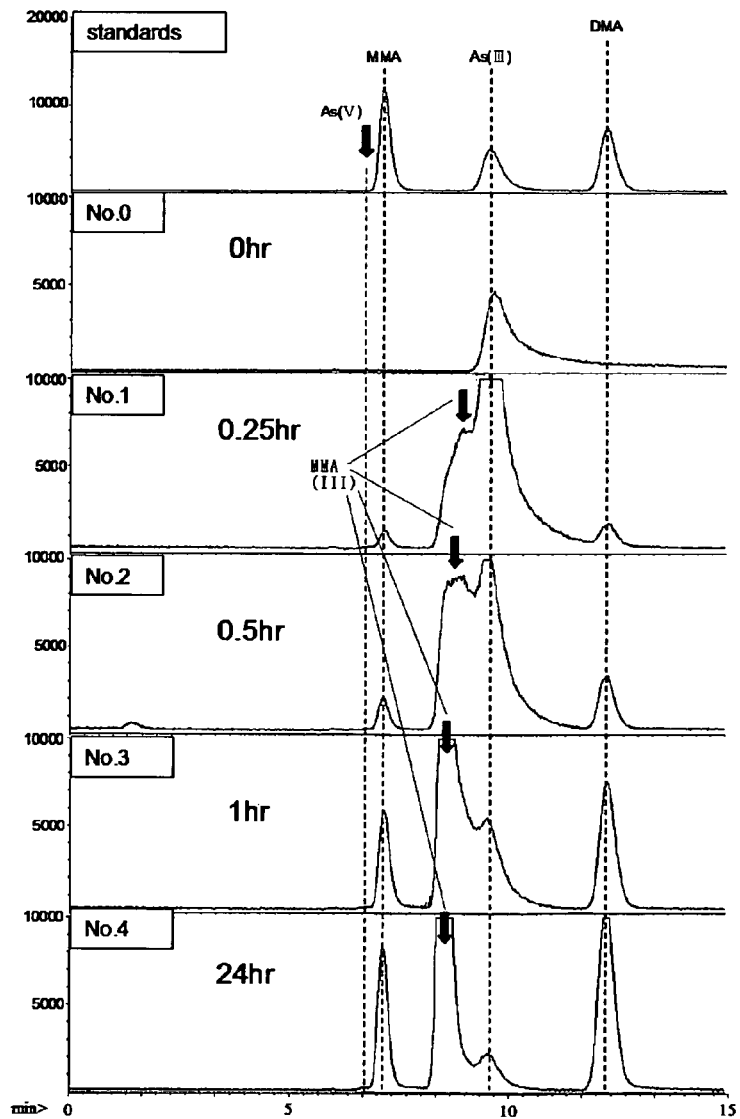

[Figure 11]
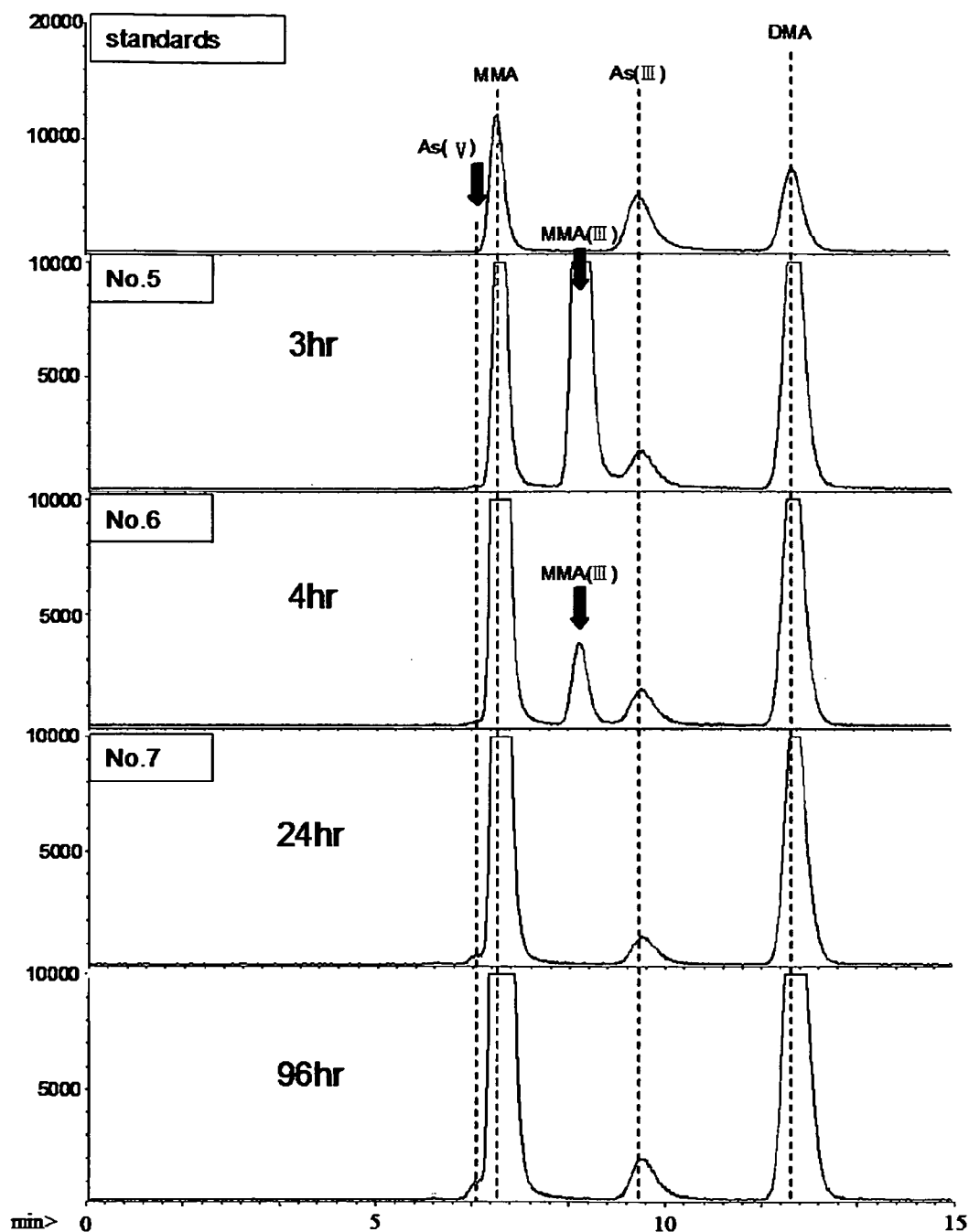

[Figure 12]
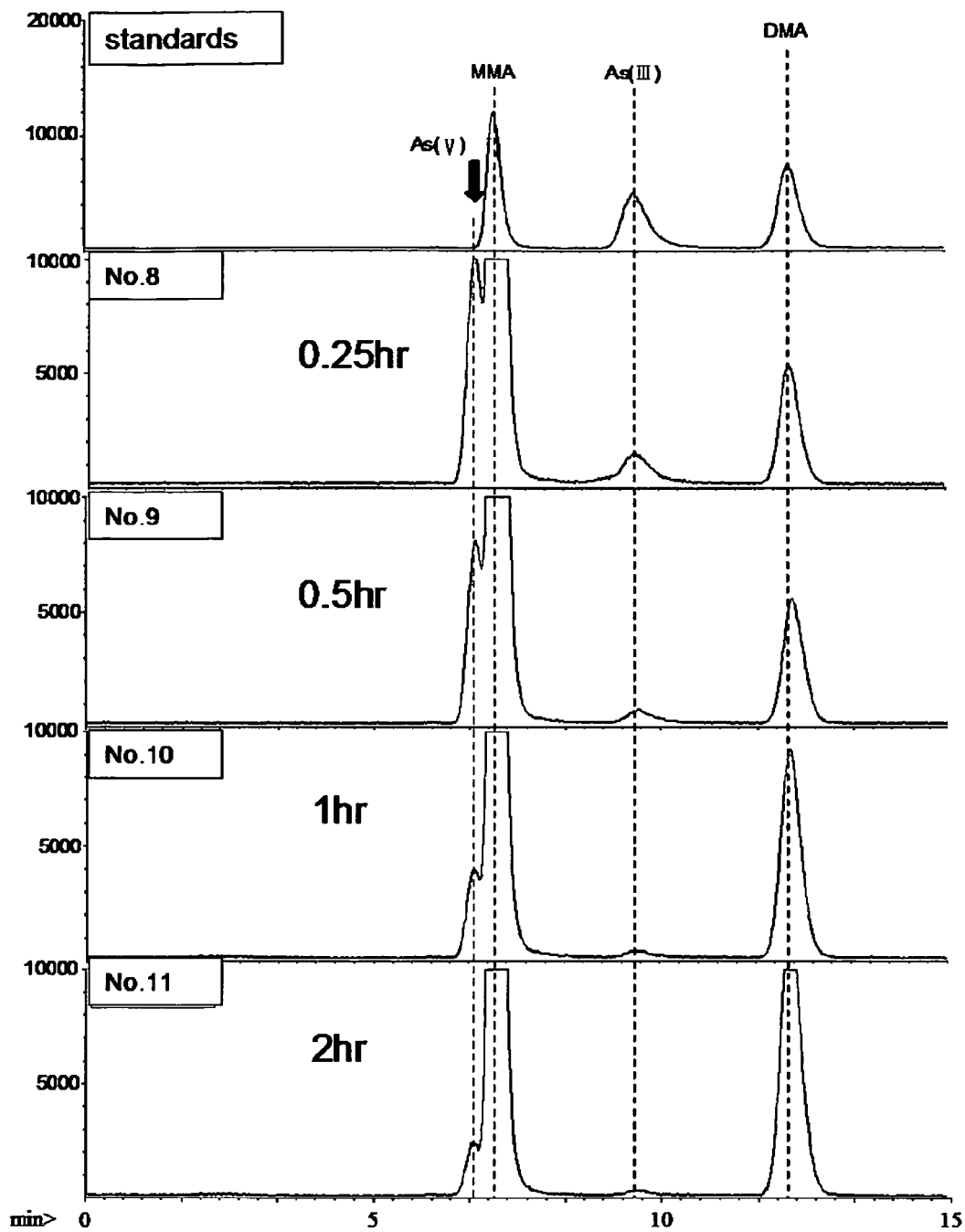

[Figure 13]
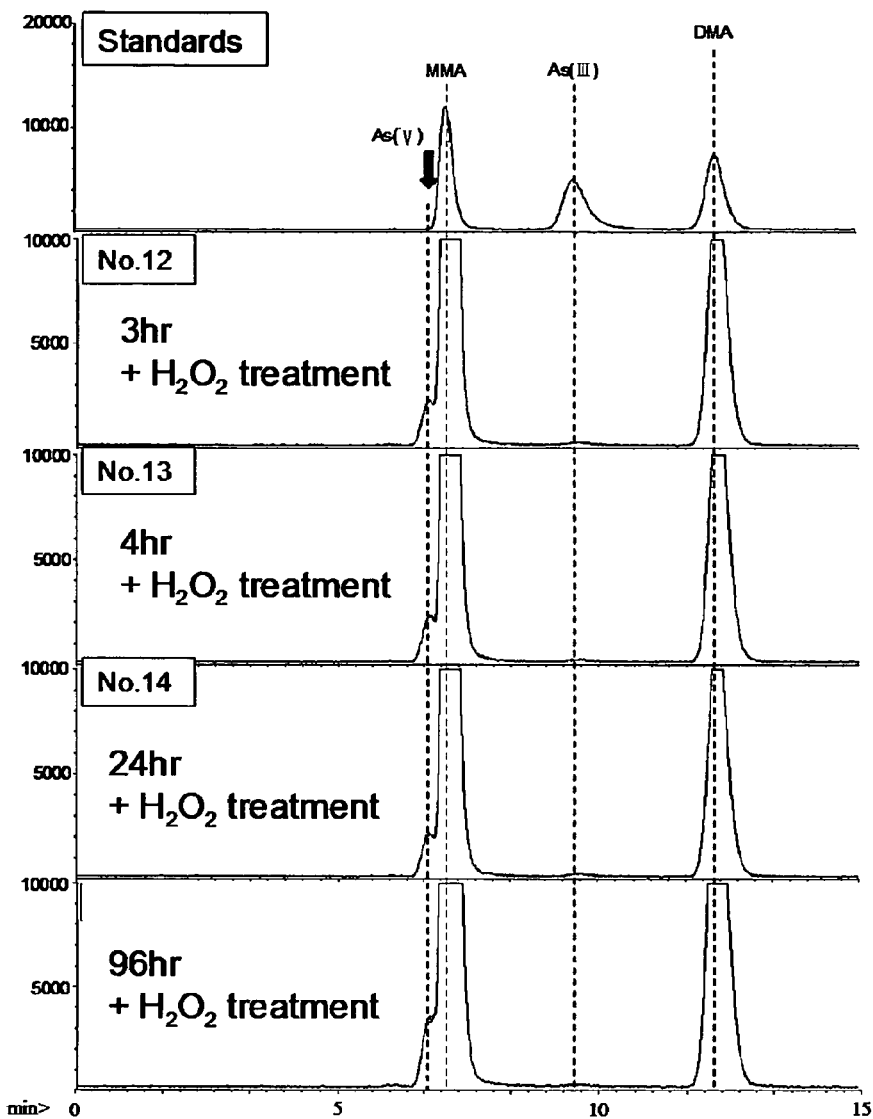
[Figure 14]
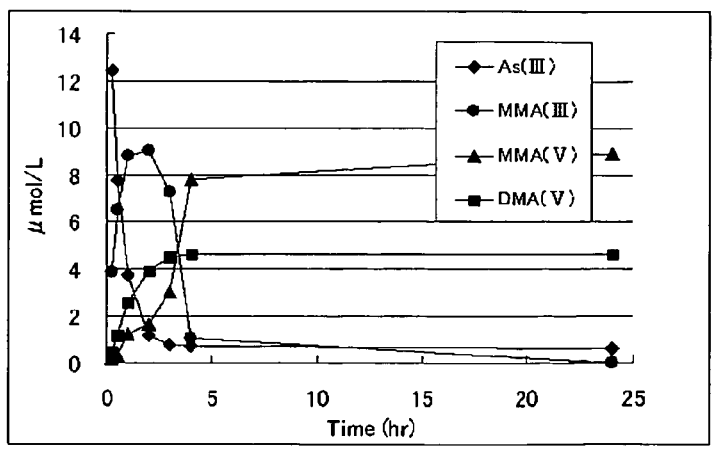

[Figure 15]
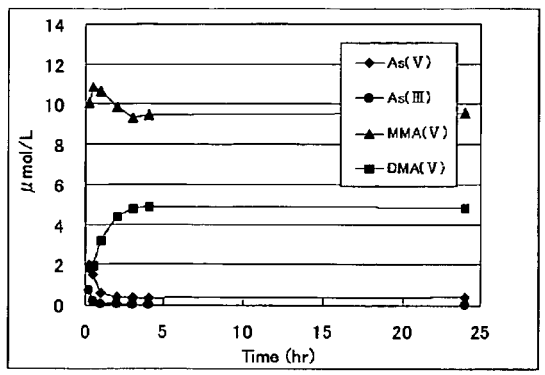
[Figure 16]
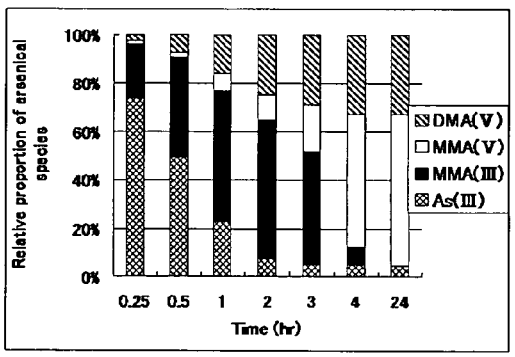
[Figure 17]
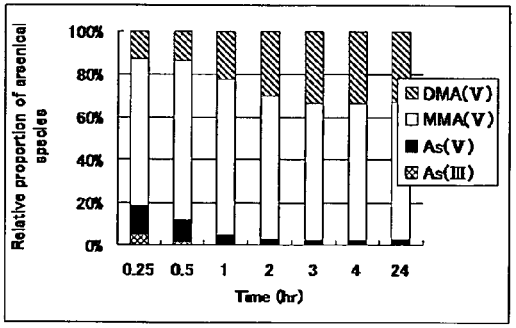
[Figure 18]
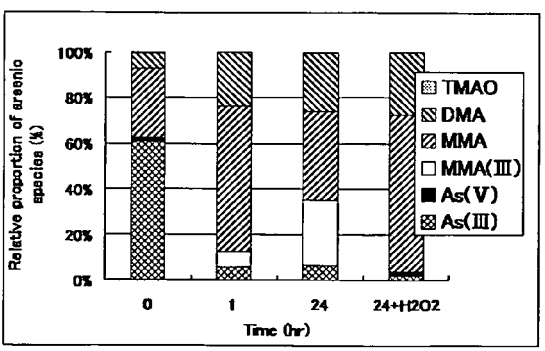

[Figure 19]
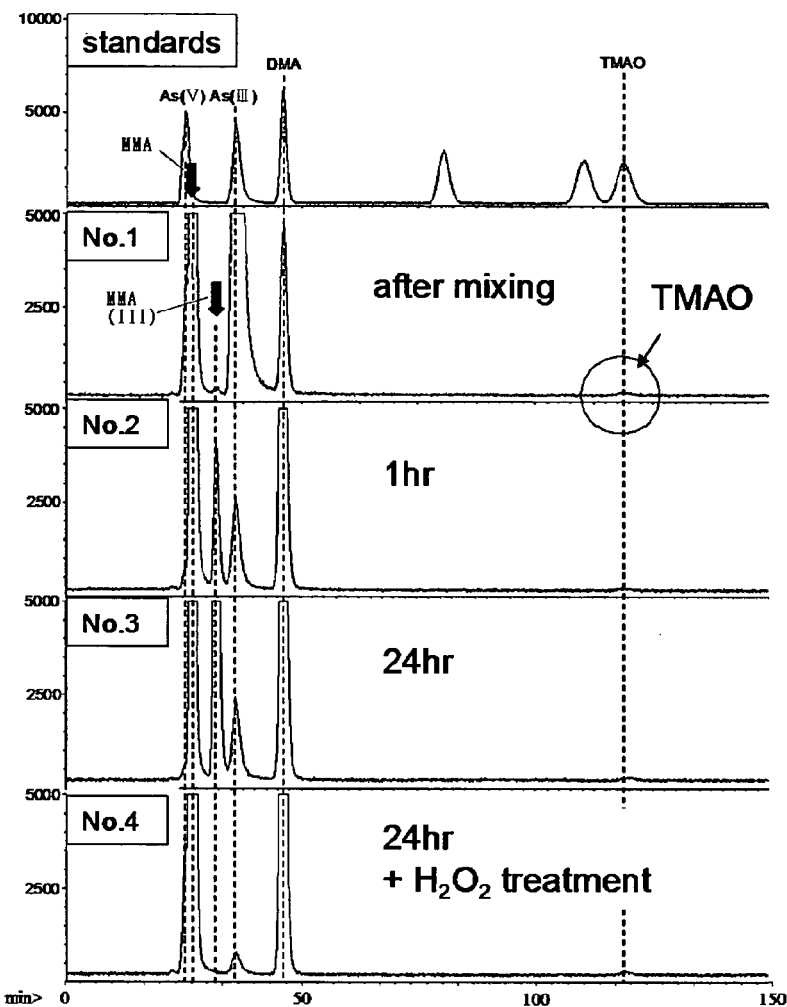
[Figure 20]
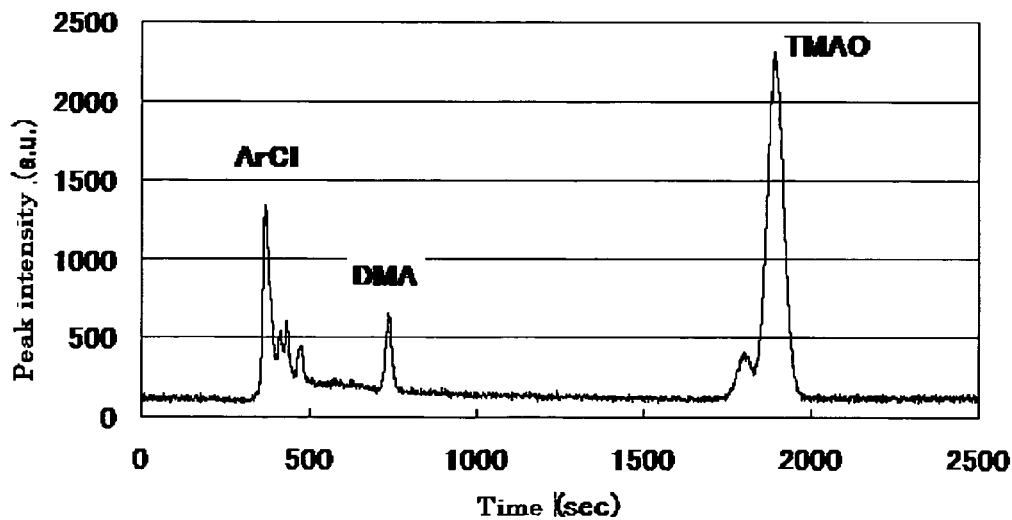

[Figure 21]
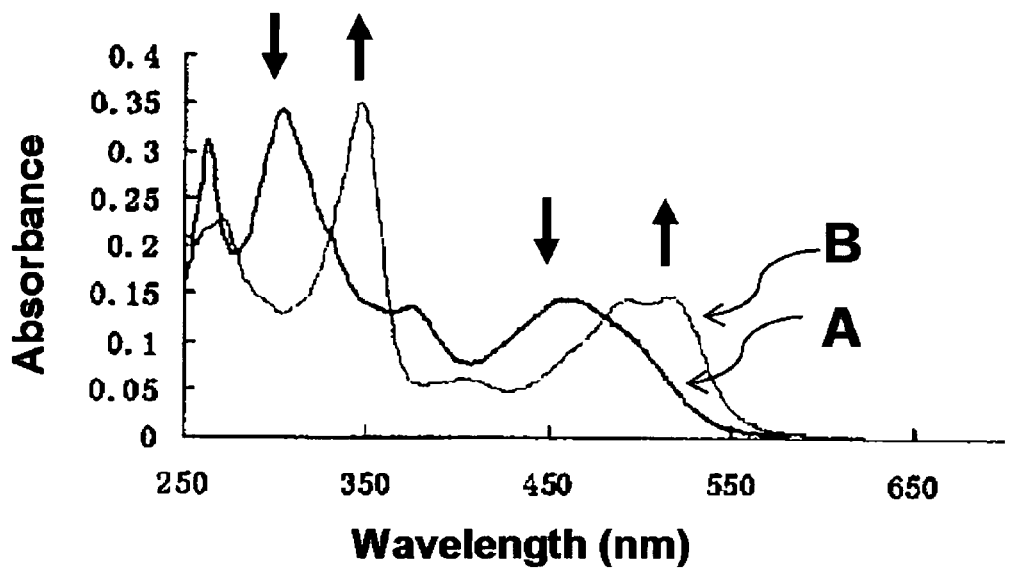
[Figure 22]
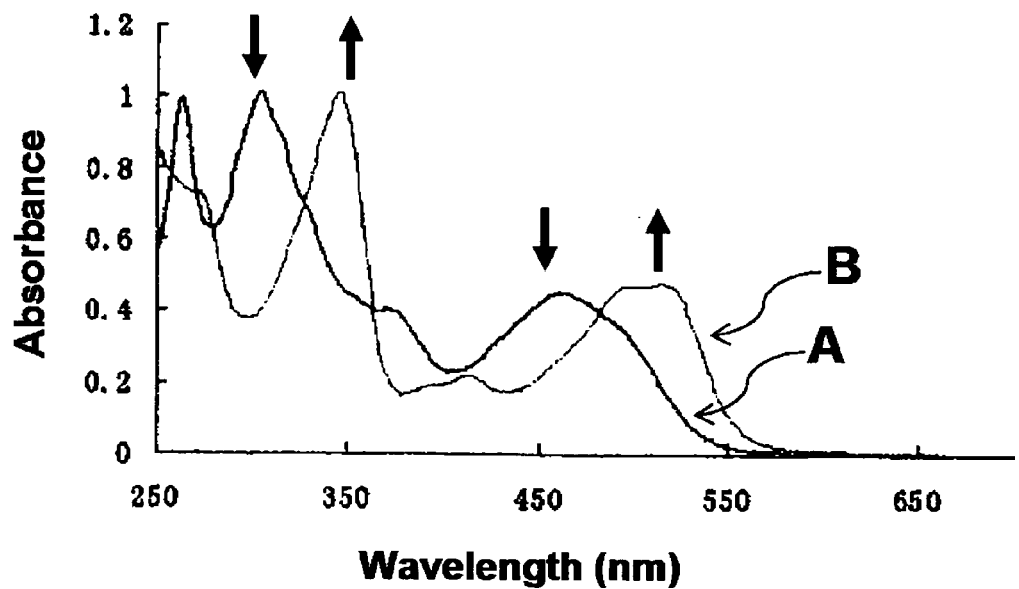

[Figure 23]
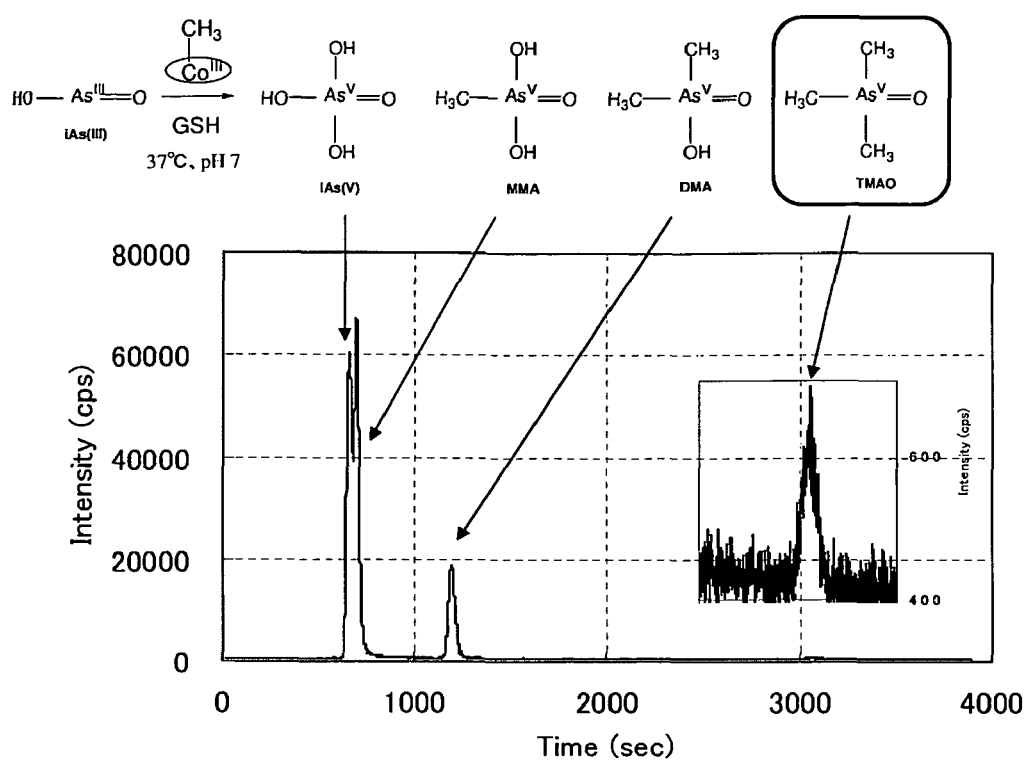

[Figure 24]
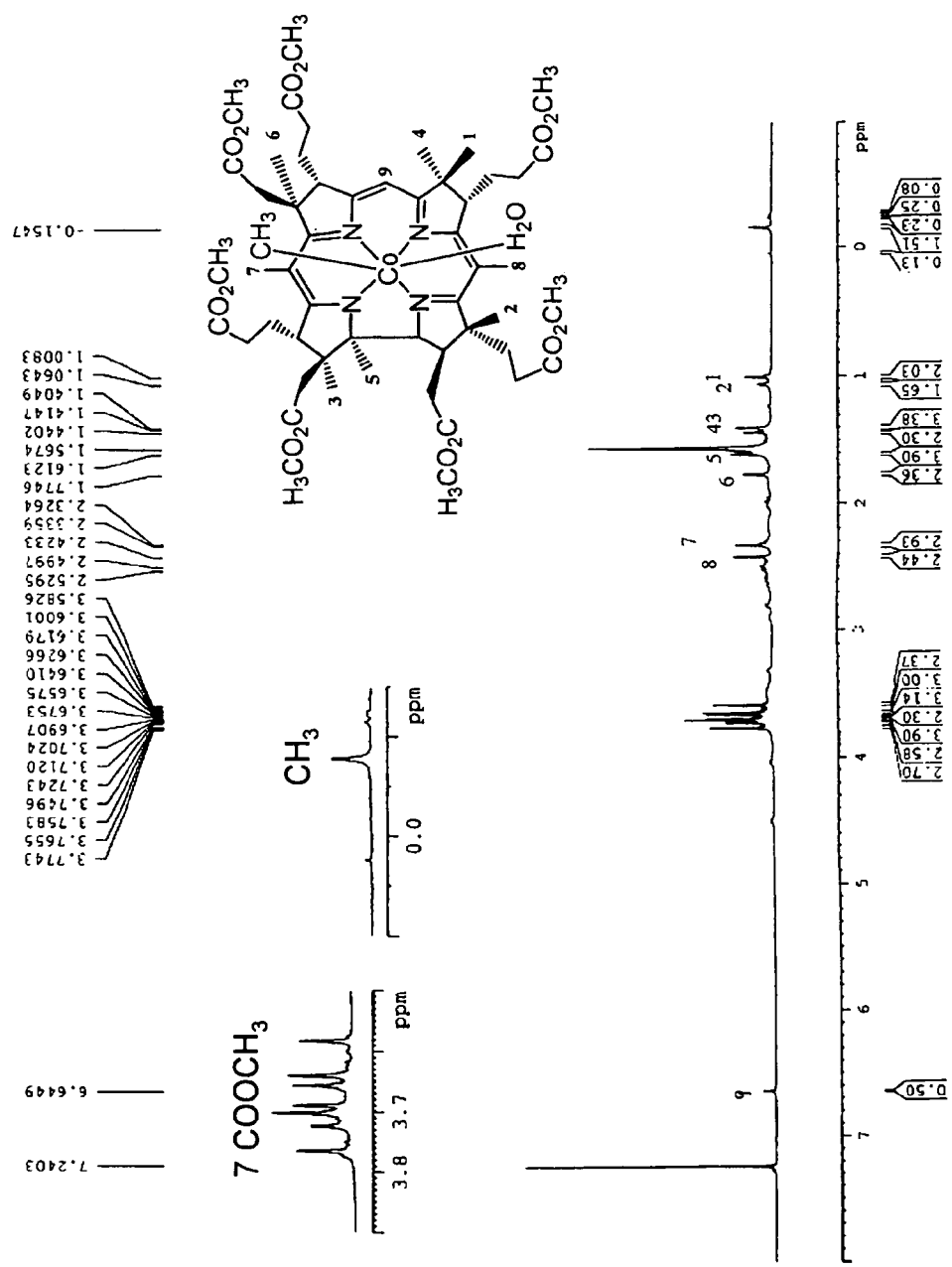

[Figure 25]
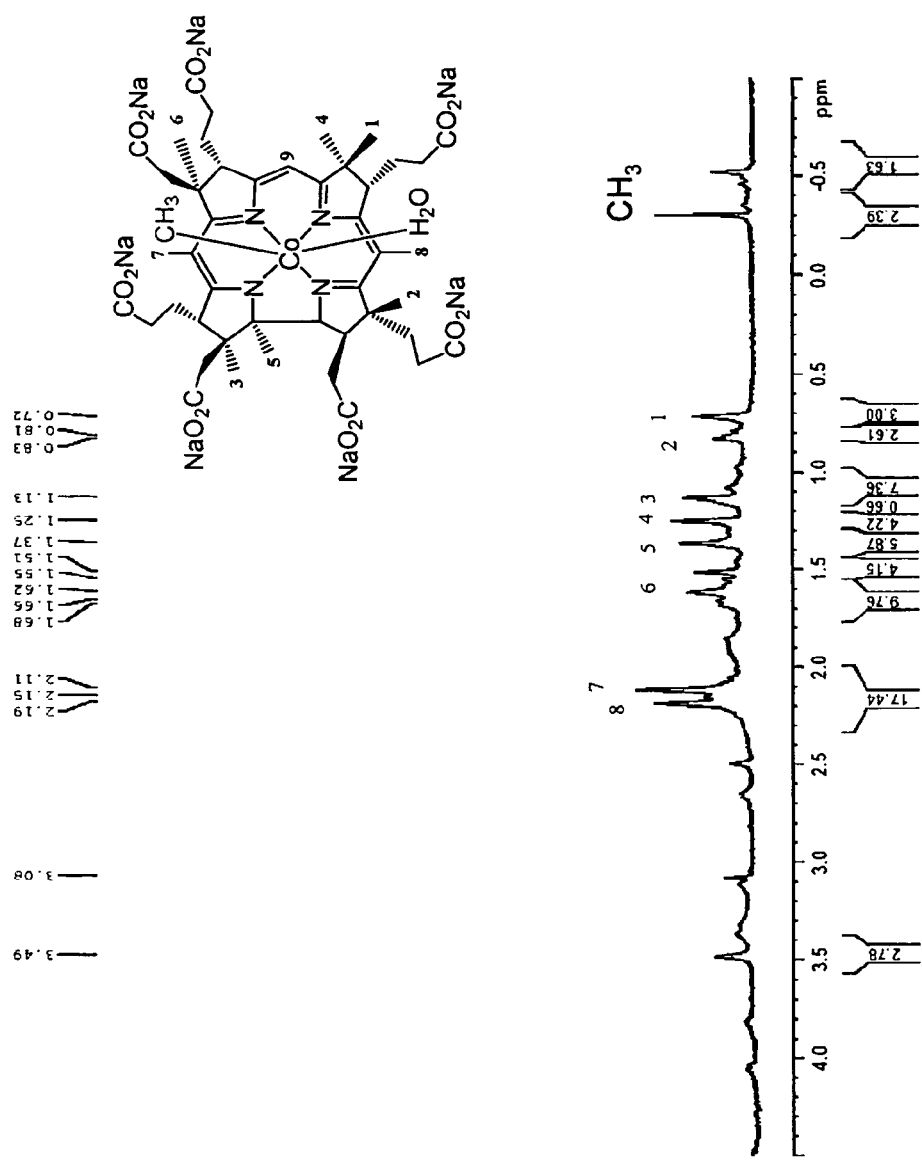

METHYL AQUOCOBYRINIC ACID DERIVATIVE, ALKYLATION COMPOSITION, AND METHOD FOR DETOXIFYING A HARMFUL COMPOUND BY UTILIZING THE COMPOSITION

TECHNICAL FIELD

The present invention relates to a methyl aquocobyrinic acid derivative, an alkylation composition, and a method for detoxifying a harmful compound by utilizing the composition.

BACKGROUND ART

The heavy metal material such as arsenic, antimony and selenium is widely used as an industrial material, for example, semiconductor, but the influence on the organism by being flowed it out into an environment is concerned, since it is harmful material for the organism.

In the past, as a method for removing these heavy metal, a method wherein a flocculating agent such as polychlorinated aluminum (PAC) is added into the wastewater containing an inorganic arsenic such as a harmful arsenous acid, and then the inorganic arsenic is removed by the filtration after the inorganic arsenic is aggregated, adsorbed to the flocculating agent and iron contained in a raw water and then precipitated, or a method wherein an arsenic compound etc. is adsorbed by using an activated alumina, cerium based flocculating agent, are generally known.

On the other hand, it is known in nature that an inorganic arsenic is stored in sea food such as a seaweed, and then a part of the inorganic arsenic is converted to an organic arsenic compound such as dimethyl arsenic by the physiological response (Nonpatent literature 1). And it is generally known that these organic arsenic compound has lower toxicity than that of the inorganic arsenic for the mammal. In particular, most of arsenic contained in the sea food exists as arsenobetaine. It is internationally recognized that arsenobetaine is a harmless substance.

Nonpatent literature 1: Kaise et al., 1998, Organomet. Chem., 12 137-143

DISCLOSURE OF THE INVENTION

Problems to be Resolved by the Invention

However, in the above method of removing the heavy metal characterized by the use of the filtration and adsorption, it is necessary to store or reclaim a polluted sludge containing the harmful compound such as the inorganic arsenic which is still harmful, and an absorbent to which the harmful compound is absorbed, under the condition of sealing off the harmful compound with the use of the concrete etc., in order to prevent it from being leaked to the outside. Therefore, there is problem that the mass disposal is difficult since a storage place or a large space for a reclaimed area are required.

Therefore, in order to resolve the above problems, it is an object of the present invention to provide a beneficial composition and a method for detoxifying a harmful compound by using said composition to detoxify the harmful compound containing arsenic etc. effectively and methodically.

Means of Solving the Problems

In order to accomplish the above objects, the present inventors made strenuous studies on the methylating reaction of the harmful compound, specifically, the methylation, especially dimethylation, and more preferably trimethylation of the harmful compound containing arsenic etc., by chemical reactions with the use of an organic metal complex having cobalt-carbon bond. As a result, the inventors discovered the present invention.

That is, the methyl aquocobyrinic acid derivative according to the present invention is characterized in that the derivative is as shown in the following general formula [Chemical 1]:

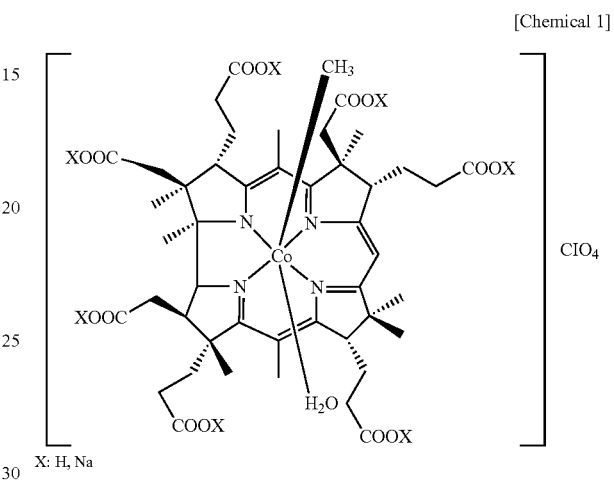

[Chemical 1]

X: H, Na (wherein X is H or Na in the formula).

A composition for the alkylation according to the present invention, wherein the composition contains an organic metal complex having cobalt-carbon bond, the organic metal complex is methyl aquocobyrinic acid derivative as shown in the general formula [Chemical 2]:

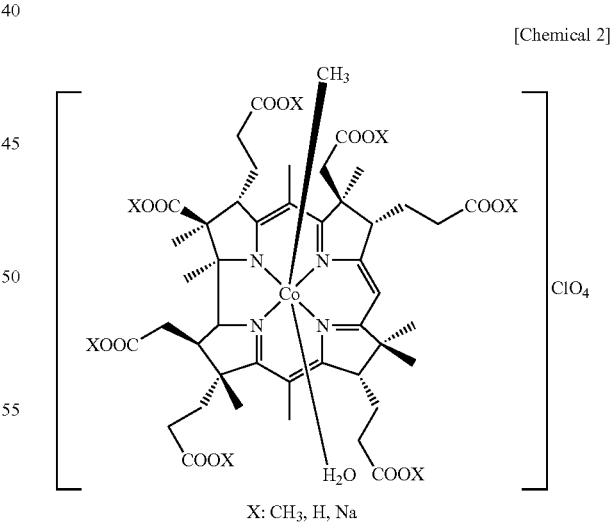

[Chemical 2]

X: CH₃, H, Na (wherein X is $CH_3$, H or Na in the formula).

Furthermore, in a preferred embodiment of the composition for the alkylation according to the present invention, wherein the organic metal complex is methyl aquocobyrinic acid heptamethyl ester perchlorate [$(CH_3)(H_2O)Cob(III)7C_1ester]ClO_4$ [Chemical 3]:

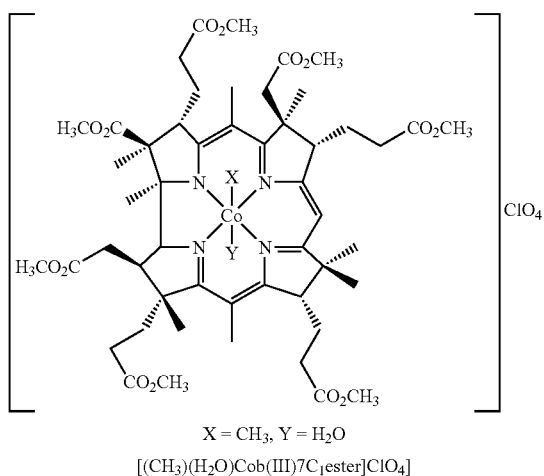

X = CH₃, Y = H₂O
[(CH₃)(H₂O)Cob(III)7C₁ester]ClO₄]

Furthermore, in a preferred embodiment of the composition for the alkylation according to the present invention, wherein the harmful compound containing at least one element selected from the groups comprising arsenic, antimony and selenium is alkylated by using the organic metal complex.

Furthermore, in a preferred embodiment of the composition for the alkylation according to the present invention, wherein the composition further contains a reducing agent to reduce at least one metal selected from the groups comprising arsenic, antimony and selenium.

Furthermore, in a preferred embodiment of the composition for the alkylation according to the present invention, wherein the reducing agent is a material having SH group.

Furthermore, in a preferred embodiment of the composition for the alkylation according to the present invention, wherein the material having SH group is at least one selected from the groups comprising glutathione, reduced glutathione (GSH), cysteine, S-adenosyl cysteine, sulforaphane, dithiothreitol and thioglycol.

Furthermore, in a preferred embodiment of the composition for the alkylation according to the present invention, wherein the composition further contains a methylating additive factor having S-Me group.

Furthermore, in a preferred embodiment of the composition for the alkylation according to the present invention, wherein the methylating additive factor is at least one selected from the groups comprising methionine and S-adenosyl methionine.

Furthermore, in a preferred embodiment of the composition for the alkylation according to the present invention, wherein the composition further contains a buffer solution.

Furthermore, in a preferred embodiment of the composition for the alkylation according to the present invention, wherein a pH of the buffer solution is in the range of 5-10.

Furthermore, in a preferred embodiment of the composition for the alkylation according to the present invention, wherein the composition further contains an organic halide compound.

Furthermore, in a preferred embodiment of the composition for the alkylation according to the present invention, wherein the organic halide compound is methyl halide.

Furthermore, in a preferred embodiment of the composition for the alkylation according to the present invention, wherein the methyl halide is at least one selected from the groups comprising methyl iodide, methyl bromide, and methyl chloride.

Furthermore, in a preferred embodiment of the composition for the alkylation according to the present invention, wherein the organic halide compound is a halogenated acetic acid.

Furthermore, in a preferred embodiment of the composition for the alkylation according to the present invention, wherein the halogenated acetic acid is at least one selected from the groups comprising chloroacetic acid, bromoacetic acid and iodoacetic acid.

Furthermore, in a preferred embodiment of the composition for the alkylation according to the present invention, wherein the organic halide compound is at least one selected from the groups comprising methyl chloride, methyl bromide, methyl iodide, chloroacetic acid, bromoacetic acid, iodoacetic acid, chloroethanol, bromoethanol, iodoethanol, chloropropionic acid, bromopropionic acid, iodopropionic acid, chloroacetic acid ethyl ester, bromoacetic acid ethyl ester, iodoacetic acid ethyl ester.

Furthermore, a method for detoxifying a harmful compound according to the present invention, wherein a harmful compound containing at least one element selected from the groups comprising arsenic, antimony and selenium is detoxified by the alkylation of the harmful compound, in the presence of the composition discussed above.

Furthermore, in a preferred embodiment of the method for detoxifying a harmful compound according to the present invention, wherein the detoxification is attained by increasing the oxidation number of a valence of the one element.

Furthermore, in a preferred embodiment of the method for detoxifying a harmful compound according to the present invention, wherein at least one bond of the one element is alkylated.

Furthermore, in a preferred embodiment of the method for detoxifying a harmful compound according to the present invention, wherein the element is arsenic.

Furthermore, in a preferred embodiment of the method for detoxifying a harmful compound according to the present invention, wherein 50% of a lethal dose ($LD_{50}$) of the compound detoxified by the alkylation is greater or equal to 1000 mg/kg.

Furthermore, in a preferred embodiment of the method for detoxifying a harmful compound according to the present invention, wherein 50% of an inhibition of cell growth concentration ($IC_{50}$) of the compound detoxified by the alkylation is greater or equal to 1000 µM.

Furthermore, in a preferred embodiment of the method for detoxifying a harmful compound according to the present invention, wherein the harmful compound is selected from the groups comprising arsenic trioxide, arsenic pentoxide, arsenic trichloride, arsenic pentachloride, arsenic sulfide compound, cyano arsenic compound, chloro arsenic compound, and the other arsenic inorganic salt.

Furthermore, in a preferred embodiment of the method for detoxifying a harmful compound according to the present invention, wherein the alkylation is a methylation.

Furthermore, in a preferred embodiment of the method for detoxifying a harmful compound according to the present invention, wherein the harmful compound is converted to a dimethyl compound, or a trimethyl compound by the methylation.

Furthermore, in a preferred embodiment of the method for detoxifying a harmful compound according to the present invention, wherein the dimethyl compound is dimethyl arsonyl ethanol (DMAE), dimethyl arsonyl acetate (DMAA), dimethylarsinic acid, or arseno sugar.

Furthermore, in a preferred embodiment of the method for detoxifying a harmful compound according to the present invention, wherein the trimethyl compound is arsenocholine, arsenobetaine, trimethyl arseno sugar, or trimethyl arsine oxide.

Effect of Invention

The composition for the alkylation according to present invention has an advantageous effect that it is possible to alkylate the harmful compound, in particular, the harmful compound containing arsenic, antimony and selenium etc., easily and simply. Furthermore, according to the method of the present invention, it has an advantageous effect that a large space such as storage place is not required since it is possible to detoxify the harmful compound without limit. Furthermore, according to the method of the present invention, it has an advantageous effect that the unnecessary byproduct is not generated since it does not use a biological material in itself in a viable condition. Furthermore, according to the present invention, it has an advantageous effect that it is possible to decrease the harmful inorganic arsenic even more with a simple method.

BRIEF DESCRIPTION OF THE DRAWINGS

FIG. 1 gives an electronic spectrum of Co(III) complex of vitamin $B_{12}$. (Solvent: methylene chloride) A shows a case of $(CN)_2Cob(III)7C_1ester$, and B shows a case of $[(CN)(H_2O)Cob(III)7C_1ester]ClO_4$, respectively.

FIG. 2 gives an electronic spectrum of Co(II) complex of vitamin $B_{12}$. (Solvent: methylene chloride) A shows a case of $[Cob(II)7C_1ester]ClO_4$ (base-off type), and B shows a case of $[Cob(II)7C_1ester]ClO_4$+pyridine (base-on type), respectively.

FIG. 3 gives an electronic spectrum of Co complex of vitamin $B_{12}$. (Solvent: methylene chloride) In FIG. 3, A shows a case of $[(CH_3)(H_2O)Cob(III)7C_1ester]ClO_4$ (Solvent: methylene chloride, before exposure to light), and B shows a case of a spectrum of A after exposure to light, respectively.

FIG. 4 gives a HPLC-ICP-MS chromatogram of a methylated reaction product of the inorganic arsenic according to $[(CH_3)(H_2O)Cob(III)7C_1ester]ClO_4$. (A) shows a case of 30 minute after reaction, (B) shows a case of 4 hours after reaction, respectively.

FIG. 5 gives a HPLC-ICP-MS chromatogram. (A No. on the graph corresponds to a No. on the table 3.)

FIG. 6 gives a HPLC-ICP-MS chromatogram. (A No. on the graph corresponds to a No. on the table 3.)

FIG. 7 gives a variation per hour of the concentration of an arsenic compound in the reaction solution. (It is in a plot as to the No. 1-8 of the table 3.)

FIG. 8 shows a variation per hour of the percentage of an arsenic compound in the reaction solution. (It is in a graph form of the No. 1-7 of the table 3.)

FIG. 9 shows a variation per hour of the percentage of an arsenic compound in the reaction solution. (It is in a graph form of the No. 6-11 of the table 3.)

FIG. 10 gives a HPLC-ICP-MS chromatogram. (A No. on the graph corresponds to a No. on the table 4.)

FIG. 11 gives a HPLC-ICP-MS chromatogram. (A No. on the graph corresponds to a No. on the table 4.)

FIG. 12 gives a HPLC-ICP-MS chromatogram (in a case of a treatment of hydrogen peroxide). (A No. on the graph corresponds to a No. on the table 4.)

FIG. 13 gives a HPLC-ICP-MS chromatogram (A No. on the graph corresponds to a No. 12-14 on the table 4).

FIG. 14 shows a variation per hour of the concentration of an arsenic compound in the reaction solution (in a case of a non-treatment of hydrogen peroxide).

FIG. 15 shows a variation per hour of the concentration of an arsenic compound in the reaction solution (after hydrogen peroxide treatment).

FIG. 16 shows a variation per hour of the percentage of an arsenic compound in the reaction solution (in a case of a non-treatment of hydrogen peroxide).

FIG. 17 shows a variation per hour of the percentage of an arsenic compound in the reaction solution (after hydrogen peroxide treatment).

FIG. 18 shows a variation per hour of the percentage of an arsenic compound in the reaction solution.

FIG. 19 gives a HPLC-ICP-MS chromatogram.

FIG. 20 gives a HPLC-ICP-MS chromatogram (corresponding to a No. 10 of the table 6, a No. 10 of the table 7 and a No. 10 of the table 8).

FIG. 21 gives an electronic spectrum of methyl aquocobyrinic acid heptamethyl ester perchlorate $[(CH_3)(H_2O)Cob(III)7C_1ester]ClO_4$. A: before exposure to light, B: after exposure to light.

FIG. 22 gives an electronic spectrum of methyl aquocobyrinic acid sodium perchlorate $[(CH_3)(H_2O)Cob(III)COONa]ClO_4$. A: Before exposure to light, B: After exposure to light.

FIG. 23 gives a HPLC-ICP-MS chromatogram.

FIG. 24 gives a $^1$H-NMR of methyl aquocobyrinic acid heptamethyl ester perchlorate $[(CH_3)(H_2O)Cob(III)7C_1ester]ClO_4$.

FIG. 25 gives a $^1$H-NMR signal in a case of methyl aquocobyrinic acid heptamethyl ester perchlorate $[(CH_3)(H_2O)Cob(III)7C_1ester]ClO_4$ is hydrolyzed.

BEST MODE FOR CARRYING OUT THE INVENTION

The methyl aquocobyrinic acid derivative according to the present invention is characterized in that the derivative is as shown in the following general formula [Chemical 4]:

[Chemical 4]

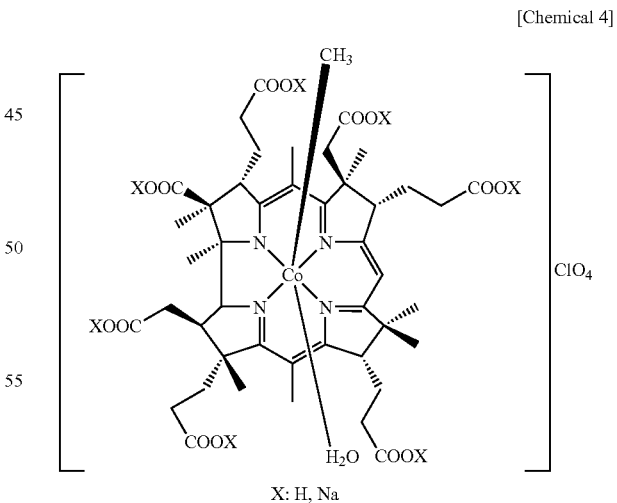

X: H, Na (wherein X is H or Na in the formula). In a preferred embodiment, X is H or Na in the above formula [Chemical 4].

Further, the composition for the alkylation according to the present invention, wherein the composition contains an organic metal complex having cobalt-carbon bond, the organic metal complex is methyl aquocobyrinic acid derivative as shown in the general formula [Chemical 5]:

[Chemical 5]

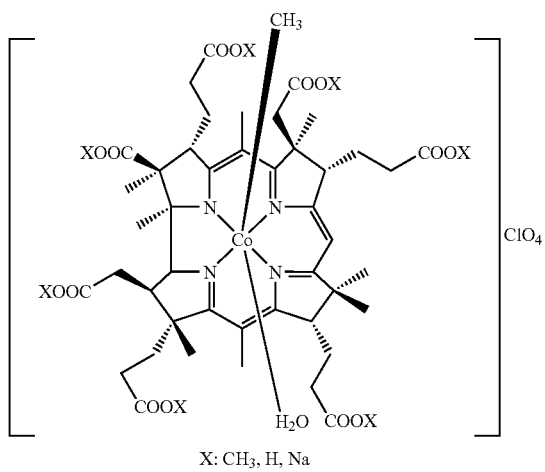

X: CH$_3$, H, Na (wherein X is CH$_3$, H or Na in the formula).

In a preferred embodiment, X is H or Na in the above formula [Chemical 5]. At this moment, the reason why X is preferably H or Na depends on a new knowledge of inventors which it is possible to convert arsenic trioxide etc., into trimethyl arsenic etc., at almost 100% yield as to the methylation of arsenic etc., because the use of those methyl aquocobyrinic acid derivative makes it possible to increase the resolvability to the solution and enhance the concentration.

That is, this is because the inventors discovered that those in the case of X=H or Na has a soluble carboxyl group, compared with in the case of X=CH$_3$ (hydrophobic vitamin B12 (cobyrinic acid heptamethyl ester) in the formula [Chemical 5], so that this makes it possible to improve the solubility and provide a condition of a high concentration in order to improve an efficient of the methylation reaction.

On the other hand, in the case of hydrophobic vitamin B12 (X=CH$_3$, in the [Chemical 5]), the compound can be also utilized from a viewpoint that the compound has a predominant benefit that (1) this makes it possible to extract it easily from the mixture of the reaction solution by the organic solvent, and to recycle it repeatedly, (2) a reactivity in the water-soluble system coexisting the organic solvent is high or equal to those of the water-soluble vitamin 12 (methyl cobalamin), as an advantageous effect of the compound.

Furthermore, in a preferred embodiment of the composition for the alkylation according to the present invention, wherein the composition contains methyl aquocobyrinic acid heptamethyl ester perchlorate [(CH$_3$)(H$_2$O)Cob(III) 7C$_1$ester]ClO$_4$ [Chemical 6], which is the organic metal complex containing cobalt-carbon bond:

[Chemical 6]

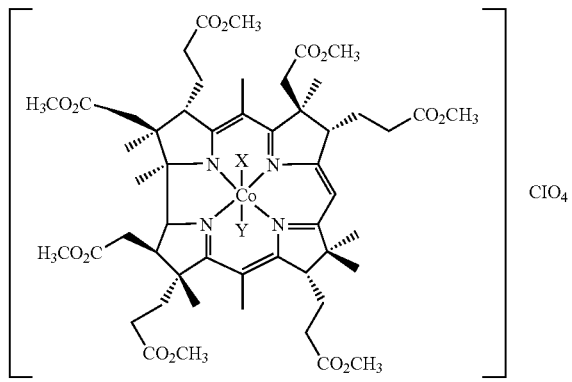

[(CH$_3$)(H$_2$O)Cob(III)$_7$C$_1$ester]ClO$_4$]
X = CH$_3$, Y = H$_2$O

Moreover, it is possible to use the above compound as the composition, even if the compound wherein the above X=H, CH$_3$ or Na can be used by itself or in combination with those compound, for example, in combination with both a compound which X=H and a compound which X=CH$_3$, both a compound which X=H and a compound which X=Na, or both a compound which X=Na and a compound which X=CH$_3$, or even if a compound containing all compound, that is, a compound which X=H, a compound which X=CH$_3$ and a compound which X=Na, can be used as the composition.

That is, in the composition for the alkylation according to the present invention, it is possible to alkylate the harmful compound containing at least one element selected from the groups comprising arsenic, antimony and selenium by using the organic metal complex. The term "the harmful compound" used herein means a compound which gives any adverse affect to the organism when it is flowed out into the environment and exposed to the organism.

As the harmful compound containing arsenic among the above harmful compound, mention may be made of arsenious acid, arsenic pentoxide, arsenic trichloride, arsenic pentachloride, arsenic sulfide compound, cyano arsenic compound, chloro arsenic compound, and other arsenic inorganic salt and or the like. In these arsenic, for example, LD$_{50}$ (50% of the fatal dose in mouse) is less or equal to 20, and therefore, it is generally a poisonous value for the organism.

Further, as a harmful compound containing antimony, mention may be made of antimony trioxide, antimony pentoxide, antimony trichloride, and antimony pentachloride and or the like.

Further, as a harmful compound containing selenium, mention may be made of selenium dioxide, selenium trioxide.

In a preferred embodiment, the composition of the present invention may further contain a reducing agent to reduce at least one metal selected from the groups comprising arsenic, antimony and selenium. The presence of the reducing agent makes it possible to further accelerate the alkylation. Although it is thought that a reducing ability for the arsenic or the transmethylation reaction are likely to be a rate controlling in the conversion to the arsenobetaine, it is thought that the conversion to the arsenobetaine etc., may be accelerated by adding those substances. As the reducing agent like this, for example, a material having the SH group may be mentioned, which may be specifically at least one selected from the groups comprising glutathione, reduced glutathione (GSH), cysteine, S-adenosyl cysteine, sulforaphane, dithiothreitol and thioglycol.

Furthermore, in a preferred embodiment of the composition for the alkylation according to the present invention, wherein the composition further contains a methylating additive factor having S-Me group. The presence of the methylating additive factor having a S-Me group makes it possible to produce more alkyl groups, and thereby, to attain more alkyation, and consequently more detoxification. As the methylating additive factor, mention may be made of at least one selected from the groups comprising methionine and S-adenosyl methionine.

Furthermore, the composition for the alkylation according to the present invention may further contain a buffer solution. Those generally used for the isolation, purification or preservation of the biomedical materials may be used as the buffer solution, and those are not particularly limited, but mention may be made of the buffer solution such as a tris buffer, a phosphate buffer, a carbonic acid buffer, and a boric acid buffer. Furthermore, in a viewpoint that it is possible to attain the detoxification more safely, a pH of the buffer solution is preferably in the range of 5-10.

Furthermore, the composition for the alkylation according to the present invention may further contain an organic halide compound. In a viewpoint that it is possible to make it easy to convert a dimethyl compound and/or a trimethyl compound to arsenobetaine, methyl halide may be recited as the organic halide compound. In a viewpoint of a high reactivity of the methylation, as the methyl halide mention may be made of at least one selected from the groups comprising methyl iodide, methyl bromide and methyl chloride.

In addition, in a viewpoint of a high reactivity of the alkylation, as the organic halide compound mention may be made of at least one selected from the groups comprising iodoacetic acid, iodoethanol, bromoacetic acid, bromoethanol, iodopropionic acid.

In a preferred embodiment, the organic halide compound may be the halogenated acetic acid. As an example of the halogenated acetic acid, mention may be made of at least one selected from the groups comprising chloroacetic acid, bromoacetic acid and iodoacetic acid.

Furthermore, in a preferred embodiment, as the organic halide compound, mention may be made of at least one selected from the groups comprising methyl chloride, methyl bromide, methyl iodide, chloroacetic acid, bromoacetic acid, iodoacetic acid, chloroethanol, bromoethanol, iodoethanol, chloropropionic acid, bromopropionic acid, iodopropionic acid, chloroacetic acid ethyl ester, bromoacetic acid ethyl ester and iodoacetic acid ethyl ester.

Next, the method of detoxifying the harmful compound according to the present invention is explained. Namely, the method of detoxifying the harmful compound according to the present invention is characterized in that the harmful compound containing at least one element selected from the groups comprising arsenic, antimony and selenium is detoxified by the alkylation of the harmful compound, in the presence of the composition for the alkylation according to the present invention as described above. At this moment, the composition for the alkylation according to the present invention, and the harmful compound used herein mean those explained above, those explanation may be applicable for the method of detoxifying the harmful compound according to the present invention.

Furthermore, in a preferred embodiment of the method of detoxifying the harmful compound according to the present invention, in the viewpoint that the 50% of an inhibition of cell growth concentration ($IC_{50}$) or the 50% of a lethal dose ($LD_{50}$) is greater, and therefore it is possible to attain more detoxification, the detoxification is preferably attained by increasing the oxidation number of a valence of the one element contained in the above harmful compound. Specifically, it is possible to increase the oxidation number of a valence of the one element by the alkylation with the use of the composition of the present invention as described above as a catalyst for the reaction. Moreover, it is preferable to convert a trivalent of the oxidation number of a valence to a pentavalent in the case that the element is arsenic or antimony, and it is preferable to convert a tetravalent of the oxidation number of a valence to a hexavalent in the case of selenium.

In the present invention, the detoxification of the harmful compound is carried out by alkylating the harmful compound. At this moment, the present invention may attain the detoxification by alkylating at least one bond of the one element contained in the above harmful compound.

Specifically, it is possible to alkylate at least one bond of the one element by carrying out the reaction with the use of the composition for the alkylation of the present invention as described above. As an alkyl group added to the one element, mention may be made of a methyl group, an ethyl group, a propyl group etc. In a viewpoint that it is possible to attain the detoxification more effectively, a methyl group is preferable as an alkyl group.

In the method of detoxifying the harmful compound according to the present invention, in a viewpoint of the safety for the living organism, the 50% of a lethal dose ($LD_{50}$) (an oral toxicity which render a 50% of the fatal dose in mouse) of the compound detoxified by the above alkylation is preferably greater or equal to 1000 mg/kg, more preferably greater or equal to 5000 mg/kg.

Furthermore, in the method of detoxifying the harmful compound according to the present invention, in a viewpoint of the safety for the living organism, the 50% of an inhibition of cell growth concentration ($IC_{50}$) of the compound detoxified by the above alkylation or arylation is preferably greater or equal to 1000 μM, more preferably greater or equal to 3000 μM. At this moment, the term "the 50% of an inhibition of cell growth concentration ($IC_{50}$)" used herein means a numerical value which gives a necessary concentration of certain substance in order to block or inhibit a 50% of the 100 cell proliferation with the use of the substance. It shows that the smaller the numerical value of $IC_{50}$, the larger the cytotoxicity. Moreover, $IC_{50}$ was calculated from a result of the examination of the cytotoxicity which gives a plasmid DNA damage under the condition at 37° C., for 24 hours. At this moment, $IC_{50}$ of each arsenic compound is shown in table 1

TABLE 1

| Arsenic compound | $IC_{50}$ (mg/cm$^3$) |
|---|---|
| iAs (III) | 0.0007 |
| iAs (V) | 0.006 |
| MMA | 1.2 |
| DMA | 0.32 |
| TMAO | >10 |
| AB | >10 |
| AC | >10 |
| TeMA | 8 |
| AS | 2 |

*50% Growth inhibition

From the table 1, it is revealed that arseno sugar (III) having a trivalent arsenic (III) has higher cytotoxicity than those of monomethylated arsenic (MMA) and dimethylated arsenic (DMA) having a pentavalent arsenic, but has lower cytotoxicity than those of monomethylated arsenic (MMA), dimethylated arsenic (DMA) having a trivalent, and arsenious acid. On the other hand, it is recognized that monomethylated arsenic (MMA), dimethylated arsenic (DMA) having a trivalent arsenic has higher cytotoxicity than that of arsenious acid (trivalent and pentavalen), but as a whole, the arsenic (V) compound having a pentavalent arsenic has higher safety for the living organism than that of the arsenic (III) compound having a trivalent arsenic in a viewpoint of the cytotoxicity.

Moreover, $LD_{50}$ of each arsenic compound is shown in table 2.

TABLE 2

| Arsesnic compound | $LD_{50}$ (g/Kg) |
| --- | --- |
| iAs (III) | 0.0345 |
| iAs (V) | 0.014~0.018 |
| MMA | 1.8 |
| DMA | 1.2 |
| TMAO | 10.6 |
| AB | >10 |
| AC | 6.5 |
| TeMA | 0.9 |

*50% Lethal dose

Furthermore, in the method of detoxifying the harmful compound according to the present invention, a biological half-life of the compound detoxified by the above alkylation is preferably less or equal to 8 hours in a viewpoint of the safety for the living organism. In the method of detoxifying the harmful compound according to the present invention, it is preferable to convert the harmful compound to the dimethyl compound or the trimethyl compound by means of the methylation in a viewpoint that they are safer and has a lower toxicity. As the dimethyl compound mention may be made of dimethyl arsonyl ethanol (DMAE), dimethyl arsonyl acetate (DMAA), dimethylarsinic acid, or arseno sugar. As the trimethyl compound mention may be made of arsenocholine, arsenobetaine, trimethyl arseno sugar, or trimethyl arsine oxide.

EXAMPLE

The present invention will be concretely explained in more detail with reference to Examples, but the invention is not intended to be interpreted as being limited to the below Examples. At first, the explanation concerning the brevity code used in the Example is as follows:

<Brevity Code>

$[(CH_3)(H_2O)Cob(III)7C_1ester]ClO_4$: methyl aquocobyrinic acid heptamethyl ester perchlorate iAs (III): trivalent inorganic arsenic MMA: monomethylated arsenic acid DMA: dimethylated arsinic acid TMAO: trimethylarsineoxide AB: arsenobetaine (trimethyl arsonium acetic acid)

DMAA: dimethyl arsonium acetic acid

AS: arsono sugar

MeCo: methylcobalamin

GSH: glutathione (reduced form)

iSe (IV): inorganic selenium (tetravalent)

MIAA: monoiodoacetic acid

<Synthesis of Cobalt Complex>

Synthesis of the $[(CH_3)(H_2O)Cob(III)7C_1ester]ClO_4$: methyl aquocobyrinic acid heptamethyl ester perchlorate (1) Synthesis of $(CN)_2Cob(III)]7C_1ester$ <Reaction Scheme>

[Chemical 7]

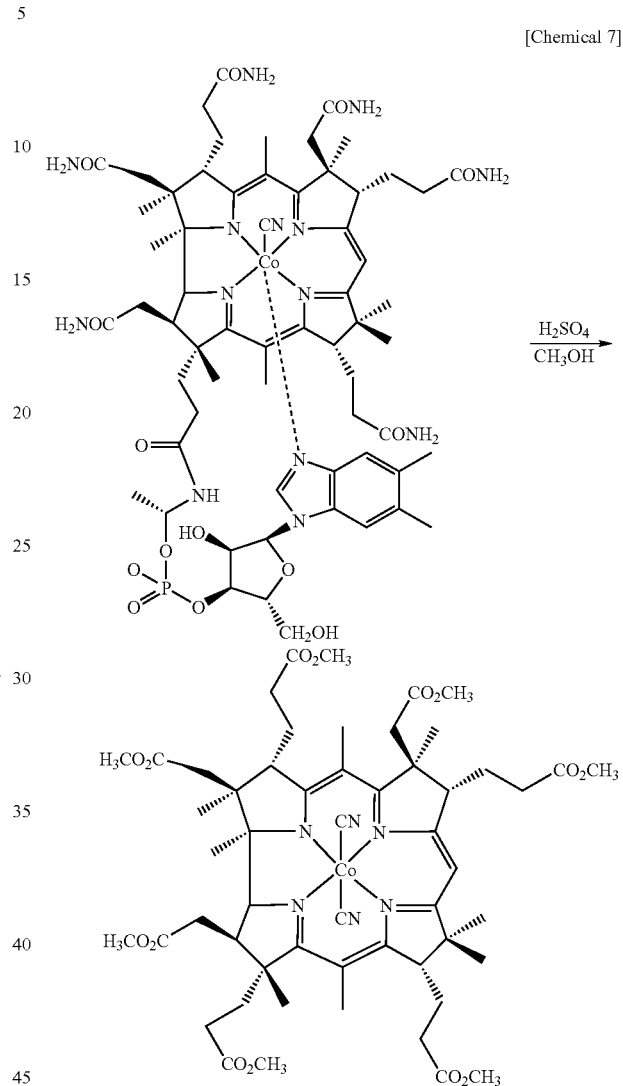

The scheme of the above [Chemical 7] shows a reaction scheme from cyanocobalamin (Left side of the Chemical 7) to $(CN)_2Cob(III)7C_1ester$ (Right side of the Chemical 7).

<Experiment Procedure>

1.0 g of cyanocobalamin ($7.5\times10^{-4}$ mol) was dissolved in 300 mL of methanol, and into a mixture obtained thus drops those containing 150 ml of methanol added 50 ml of a cold concentrated sulfuric acid, followed by a mixture obtained thus was heated to reflux for 120 hours under light shielding condition and under nitrogen atmosphere. After that, the reaction mixture was condensed under reduced pressure, and then was added 100 mL of a cold water and was neutralized with solid sodium carbonate. To this was added 4.0 g of potassium cyanide ($6.1\times10^{-2}$ mol), and was extracted with carbon tetrachloride (150 mL×3). Further, this was extracted with methylene chloride (150 mL×3). The above operation was conducted again because methylene chloride extract contains incomplete ester compounds. A carbon tetrachloride extract was dried with sodium sulfate, and then it was dried under reduced pressure. Reprecipitation of them was carried out with benzene/n-hexane (1:1 v/v) to obtain a purple powder. (Yield point: 777 mg ($7.1 \times 10^{-4}$ mol), Yield: 95%)

<Confirmation>

Mp: 138-140° C., Point of decomposition: 193-196° C. An electronic spectrum is shown in A of FIG. 1. IR (KBr pellet method): v (C≡N) 2130; v (esterC═O) 1725 cm$^{-1}$ An elemental analysis:

Actual measurement value: C, 58.46; H, 6.74; N, 7.58% $C_{54}H_{73}CoN_6O_{14} \cdot H_2O$ Calculated value: C, 58.58; H, 6.83; N, 7.59%

FIG. 1 shows an electronic spectrum of Co(III) complex of vitamin $B_{12}$. (Solvent: methylene chloride) A shows a case of $(CN)_2Cob(III)7C_1ester$, and B shows a case of $[(CN)(H_2O)Cob(III)7 C_1ester]ClO_4$, respectively.

(2) Synthesis of $[(CN)(H_2O)Cob(III)7C_1ester]ClO_4$

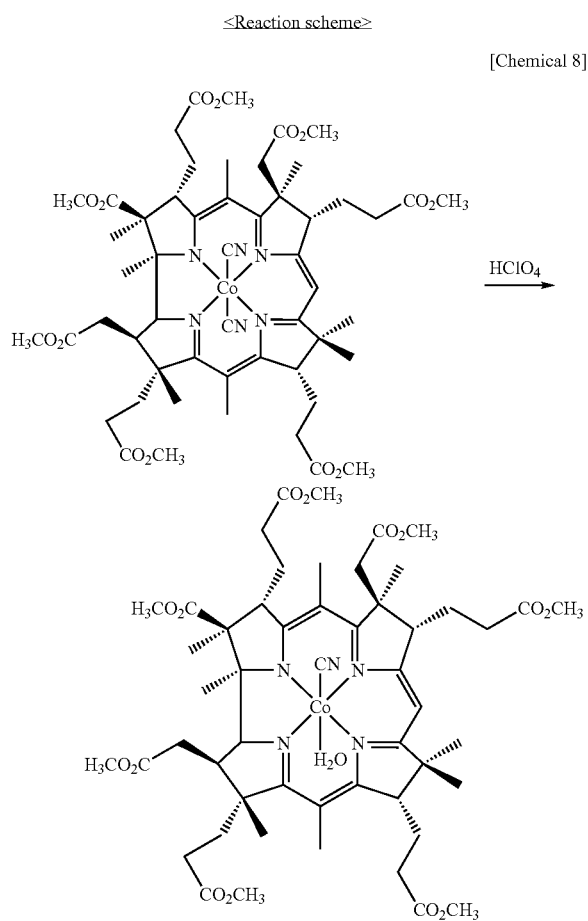

The reaction scheme of the above [Chemical 8] shows a reaction from $(CN)_2Cob(III)7C_1ester$ to $[(CN)(H_2O)Cob(III)7C_1ester]ClO_4$.

<Experiment Procedure>

50 mg of $(CN)_2Cob(III)7C_1ester$ ($4.6 \times 10^{-5}$ mol) was dissolved in 100 mL of methylene chloride, and agitated by using 30% of $HClO_{4aq.}$ and a separating funnel. A mixture was washed with water, and was dried with anhydrous sodium sulfate, and then was dried under reduced pressure. This was re-precipitated with benzene/n-hexane to obtain a powder with a red color. (Yield point: 50 mg ($3.9 \times 10^{-5}$ mol), Yield: 92%)

<Confirmation>

Mp: 96-98° C., Point of decomposition: 216-220° C. An electronic spectrum is shown in B of FIG. 1. IR (KBr pellet method): v (C≡N) 2150; v (esterC═O) 1730 cm$^{-1}$ An elemental analysis:

Actual measurement value: C, 53.75; H, 6.40; N, 6.03% $C_{54}H_{75}CoN_6O_{19}$

Calculated value: C, 53.92; H, 6.40; N, 5.93%

(3) Synthesis of $[Cob(II)7C_1ester]ClO_4$

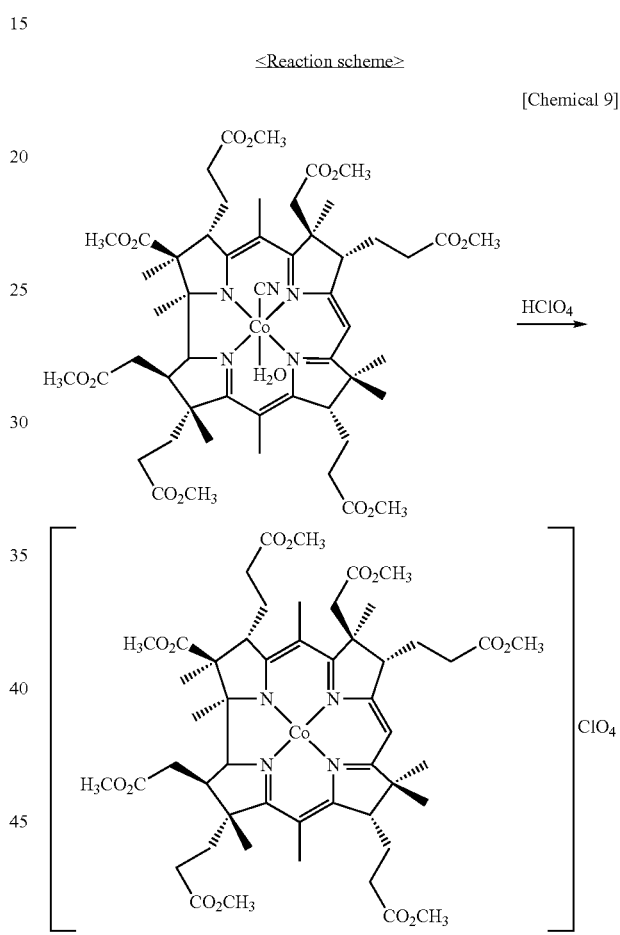

The reaction scheme of the above [Chemical 9] shows a reaction from $(CN)(H_2O)Cob(III)7C_1ester$ to $[Cob(II)7C_1ester]ClO_4$.

<Experiment Procedure>

50 mg of $(CN)(H_2O)Cob(III)7C_1ester$ ($4.2 \times 10^{-5}$ mol) was dissolved in 100 mL of methanol, and was deaerated by a nitrogen bubbling. To this was added 400 mg of $NaBH_4$ (1.05 mol) to confirm a green color derived from Co(I). To this was added 3 ml of 60% $HClO_{4aq.}$. To this was added 50 mL of water and was extracted with methylene chloride. A mixture was washed with water, and was dried with anhydrous sodium sulfate, and then was dried under reduced pressure. This was re-precipitated with benzene/n-hexane to obtain a powder with an orange color. (Yield point: 50 mg ($3.7 \times 10^{-5}$ mol), Yield: 87%)

<Confirmation>

Mp: 96-100° C., Point of decomposition: 190° C. An electronic spectrum is shown in A of FIG. 2. IR (KBr pellet method): v (C≡N) 2150; v (esterC=O) 1725 cm$^{-1}$; v (ClO$_4$−) 1100, 620 cm$^{-1}$ An elemental analysis:

Actual measurement value: C, 54.68; H, 6.41; N, 5.00% C$_{52}$H$_{73}$CoN$_4$O$_{18}$ Calculated value: C, 54.95; H, 6.47; N, 4.93%

(4-1) Synthesis of [(CH$_3$)(H$_2$O)Cob(III)7C$_1$ester]ClO$_4$

<Reaction scheme>

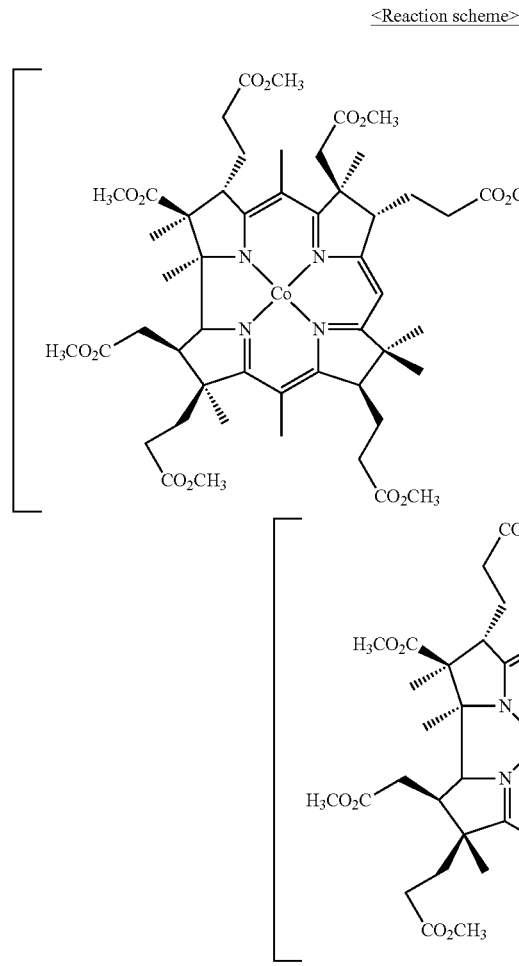

[Chemical 10]

The reaction scheme of the above [Chemical 10] shows a reaction from [Cob (II)7C$_1$ester]ClO$_4$ to [(CH$_3$)(H$_2$O)Cob(III)7C$_1$ester]ClO$_4$.

<Experiment Procedure>

30 mg of [Cob(II)7C$_1$ester]ClO$_4$ (2.6×10$^{-5}$ mol) was dissolved in 100 mL of methanol, and was deaerated by a nitrogen bubbling. To this was added 300 mg of NaBH$_4$ (0.788 mol) to confirm a green color derived from Co(I). To this was added 37 mg of CH$_3$I (2.6×10$^{-4}$ mol) and wad stirred for 5 minute. To this was added 2 mL of 60% HClO$_{4aq}$. To this was added 50 mL of water, and was extracted with methylene chloride. After a mixture was washed with water, and was dried with anhydrous sodium sulfate, and then was dried under reduced pressure. This was re-precipitated with benzene/n-hexane to obtain a powder with an orange color [(CH$_3$)(H$_2$O)Cob(III)7C$_1$ester]ClO$_4$. An electronic spectrum is shown in FIG. 3 (A: before exposure to light, B: after exposure to light). The synthesis of a methyl complex was confirmed because a cleavage of methyl group of Co-Me was confirmed by the exposure to light.

(4-2) Synthesis of [(CH$_3$)(H$_2$O)Cob(III)7C$_1$ester]ClO$_4$

<Experiment Procedure>

50 mg of [Cob(II)7C$_1$ester]ClO$_4$ (4.4×10$^{-5}$ mol) was dissolved in 30 mL of acetic acid, and was deoxygenated by a nitrogen bubbling. After that, to this was added 600 mg of a zinc powder and was stirred under a nitrogen gas stream for 10 minutes. After a color of a solution obtained thus wad changed to a dark green color under a dark place, to this was added 1.0 g of CH$_3$I (7.0×10$^{-3}$ mol) and was stirred for 5 minutes. After the reaction was terminated, a zinc powder was filtered out, 50 mL of 15% HClO$_{4aq}$ was added to a filtrate. This was extracted with methylene chloride (50 mL×three times). After an extraction was washed with 5% (w/w) sodium hydrogen carbonate solution and a distilled water, and was dried with anhydrous sodium sulfate, and then was dried under reduced pressure. This was re-precipitated with benzene/n-hexane to obtain a powder with an orange color, 43 mg (84%) of [(CH$_3$)(H$_2$O)Cob(III)7C$_1$ester]ClO$_4$.

<Confirmation>
IR (KBr pellet method): ν (esterC=O) 1730 cm$^{-1}$; ν (ClO$_4$-) 1100, 620 cm$^{-1}$ 1H-NMR(CD$_3$OD, TMS): δ −0.18 (3H, s, CH$_3$—Co)

An elemental analysis:

Actual measurement value: C, 54.49; H, 6.61; N, 4.96% C$_{53}$H$_{78}$ClCoN$_4$O$_{19}$ Calculated value: C, 54.43; H, 6.72; N, 4.80%

FIG. 2 gives an electronic spectrum of Co(II) complex of vitamin B$_{12}$ (Solvent: methylene chloride). A shows in the case of [Cob(II)7C$_1$ester]ClO$_4$ (base-off type), and B shows in the case of [Cob(II)7C$_1$ester]ClO$_4$+Pyridine (base-on type), respectively. FIG. 3 gives an electronic spectrum of Co complex of vitamin B$_{12}$ (Solvent: methylene chloride). In FIG. 3, A shows in the case of [(CH$_3$)(H$_2$O)Cob(III)7C$_1$ester]ClO$_4$ (Solvent: methylene chloride, before exposure to light), and B shows an spectrum of A after exposure to light, respectively.

Example 1

<Reaction scheme>

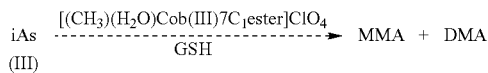

<Reacting Operation>

Into a 1.5 mL of Eppendorf tube 740 μL of a reaction buffer solution (100 mM Tris-HCl (pH7.8)) was added. To this was added 220 μL of 100 mM GSH aqueous solution, and stirred with Voltex for 30 seconds. Further to this was added 20 μL of 1000 ppm inorganic selenium (Se) (IV) standard solution (for the atomic absorption). This solution was left at rest for 60 minutes at 37° C. To this was added 20 μL of 100 ppm inorganic arsenic (III) standard solution (for the atomic absorption) and stirred for 30 seconds. To this was added 20 μL of 7.4 mM methanol solution of [(CH$_3$)(H$_2$O)Cob(III)7C$_1$ester]ClO$_4$ (methyl aquocobyrinic acid heptamethyl ester perchlorate) (Composition A). This was reacted in a constant temperature bath maintained at 37° C., the increasing amount of the product obtained with sampling at regular intervals was examined.

<Analysis of the Product>

The qualitative and quantitative analysis was carried out by using the inductively-coupled plasma ion mass spectroscope (Agilent 7500ce) directly connected to the high-performance liquid chromatography (Agilent 1100) online with the retention time of the standard sample compared with that of the reaction product. FIG. 4 gives a HPLC-ICP-MS chromatogram.

(4) Condition of Analysis

As a standard sample of the organic arsenic compound, MMA, DMA, TMAO, TeMA, AB and AC which is commercially available reagent from Optronics Co., Ltd. (trichemical research institution) and as a standard sample of an inorganic arsenic, sodium salt of As(III), As(V) which is commercially available high quality reagent from Wako Pure Chemical Industries, Ltd., were used. A standard solution of 100 mg/100 mL of each arsenic compound was prepared by diluting it with an ultrapure water (Millipore).

A condition of ICP-MS apparatus is as follows:
RF forward power: 1.6 kW
RF reflect power: <1 W
Carrier gas flow: Ar 0.75 L/min
Sampling 8.5 mm
Monitoring mass: m/z=75 and 35 internal standard m/Z=71
Dwell time: 0.5 sec 0.01 sec 0.1 sec
Times of scan: 1 time Further, a condition of HPLC is as follows:
Eluent: 5 mM nitric acid/6 mM ammonium nitrate/1.5 mM pyridine dicarboxylic acid
Flow rate of eluent: 0.4 mL/min.
Injection volume: 20 μL
Column: cation-exchange column Shodex RSpak NN-414 (150 mm×4.6 mm i.d.)
Column temperature: 40° C.

FIG. 4 gives a HPLC-ICP-MS chromatogram of a methylated reaction product of the inorganic arsenic according to [(CH$_3$)(H$_2$O)Cob(III)7C$_1$ester]ClO$_4$. (A) shows a case of 30 minute after reaction, and (B) shows a case of 4 hours after reaction, respectively. It is clear as shown in FIG. 4 that the harmful inorganic trivalent arsenic [iAs (III)] was converted to MMA and DMA which has low toxicity according to the [(CH$_3$)(H$_2$O)Cob(III)7C$_1$ester]ClO$_4$.

Comparative Example 1

The experiment was carried out in the same manner as in Example 1, except of no addition of [(CH$_3$)(H$_2$O)Cob(III)7C$_1$ester]ClO$_4$ in Example 1 (Composition B). As a result of this, any productions of methylation substances was not confirmed.

As shown in the Example 1, a methylated arsenic (MMA) and a dimethylated arsenic (DMA) was produced as time advances compared with the comparative example 1. Under the existence of [(CH$_3$)(H$_2$O)Cob(III)7C$_1$ester]ClO$_4$, a remarkable effect was confirmed that the harmful inorganic arsenic was detoxified and converted to methylated arsenic and dimethylated arsenic which have a low toxicity.

Example 2

Into a 1.5 mL of Eppendorf tube 8.6 mg of methyl aquocobyrinic acid heptamethyl ester perchlorate [(CH$_3$)(H$_2$O)Cob(III)7C$_1$ester]ClO$_4$ [Chemical 1] was collected. To this was added 1 mL of an ultrapure water (18 MΩ/cm) to dissolve methyl aquocobyrinic acid heptamethyl ester perchlorate [(CH$_3$)(H$_2$O)Cob(III)7C$_1$ester]ClO$_4$ [Chemical 1] (7.4 mmol/L) (Solution A). Into a 1.5 mL of Eppendorf tube 30.7 mg of gutathione (reduced form) was added and dissolved in 1 mL of an ultrapure water (100 mmol/L) (Solution B). An arsenic trioxide aqueous solution was prepared (for the atomic absorption: 100 ppm: as a metal arsenic) (Solution C). A selenious acid aqueous solution was prepared (for the atomic absorption: 1000 ppm: as a metal selenium) (Solution D). 100 mmol/L Tris-HCl buffer solution was prepared (pH 7.8, 0.01 mol/L, pH was controlled by hydrochloric acid solution) (Solution E). Into a 1.5 mL of Eppendorf tube, 720 μL of the solution E, 20 μL of the solution C and 220 μL of the solution D were added and left at rest for 1 hour at 37° C. To this added 20 μL of the solution A and 20 μL of the solution B were added and reacted in a constant temperature bath maintained at 37° C. (Table 3). Table 3 shows a concentration of the arsenic compound in the reaction solution.

TABLE 3

| | | Concentration (μmol/L) | | | | | |
|---|---|---|---|---|---|---|---|
| No. | Time (hr) | As (III) | As (V) | MMA (III) | MMA (V) | DMA (V) | Total |
| 1 | 0 | 30 | 0 | 0 | 0 | 0 | 30 |
| 2 | 0.5 | 18.937 | 0.027 | 1.876 | 4.189 | 1.293 | 26.293 |
| 3 | 1 | 14.377 | 0.009 | 1.981 | 5.816 | 1.995 | 25.420 |
| 4 | 2 | 12.944 | 0.005 | 3.267 | 5.463 | 2.668 | 25.657 |
| 5 | 4 | 11.584 | 0.024 | 3.819 | 5.948 | 2.999 | 25.645 |
| 6 | 21 | 8.539 | 0.205 | 1.969 | 8.945 | 2.995 | 24.796 |
| 7 | 48 | 7.509 | 0.397 | 0.029 | 10.899 | 2.971 | 23.333 |
| 8 | 72 | 3.451 | 0.077 | 0.000 | 4.947 | 1.437 | 16.856 |
| 9 | 21 | 0.000 | 4.311 | 0.000 | 13.960 | 3.185 | 20.748 |
| 10 | 48 | 0.000 | 4.352 | 0.000 | 13.147 | 3.077 | 20.299 |
| 11 | 72 | 0.000 | 3.269 | 0.000 | 9.029 | 2.181 | 13.752 |

*No. 1-8 were those of no treatment of hydrogen peroxide, and No. 9-11 were those after treated by hydrogen peroxide.

The qualitative and quantitative analysis was carried out by using the HPLC-ICP-MS method with sampling 50 μL of the product at regular time intervals and diluting the collected sample tenfold by the ultrapure water (No. 1-8 of Table 3). Further, 50 μL of the reaction solution was collected as a sample, and this was treated with 50 μL of hydrogen peroxide aqueous solution (at 37° C., for 1 hour), and was diluted tenfold by the ultrapure water, the reaction product was analyzed in the same way (No. 9-11 of Table 3). The HPLC-ICP-MS chromatograms are shown in FIGS. 5 and 6. A change in concentration of the arsenic compound in the reaction solution is shown in FIG. 7. A composition percentage of an arsenic compound is shown in FIGS. 8 and 9.

Moreover, the reaction conditions are as follows:
A concentration of the substrate: [As]=30 μmol/L
A concentration of an artificial vitamin 12: [MeCo]=150 μmol/L
A concentration of glutathione (reduced form): [GSH]=22 mmol/L
A concentration of selenium: [Se]=760 μmol/L
A buffer solution: 100 mM Tris-HCl buffer solution (pH7.8),
A reaction temperature: 37° C.

FIG. 5 gives a HPLC-ICP-MS chromatogram (A No. on the graph corresponds to a No. on the table 3). FIG. 6 gives a HPLC-ICP-MS chromatogram (A No. on the graph corresponds to a No. on the table 3). FIG. 7 gives a variation per hour of the concentration of an arsenic compound in the reaction solution (It is in a plot as to the No. 1-8 of the table 3). FIG. 8 shows a variation per hour of the percentage of an arsenic compound in the reaction solution (It is in a graph form of the No. 1-7 of the table 3). FIG. 9 shows a variation per hour of the percentage of an arsenic compound in the reaction solution (It is in a graph form of the No. 6-11 of the table 3).

Example 3

The experiment was carried out in the same manner as in Example 2, except that the solution B was added in first, and then the solution A was added. The reaction products were sampled at regular time intervals, and were analyzed by the HPLC-ICP-MS. The samples of the experimental numbers 1-7 shown in Table 4 were diluted without modification and were analyzed. The samples of the experimental numbers 8-14 shown in Table 4 were treated with hydrogen peroxide solution and were analyzed as shown in the Example 2. 95% or more of the inorganic arsenic was methylated as it is clear from Table 4, FIGS. 10-17.

TABLE 4

| | | Concentration (μmol/L) | | | | | |
|---|---|---|---|---|---|---|---|
| No. | Time (hr) | As (V) | MMA (V) | MMA (III) | As (III) | DMA (V) | Total |
| 1 | 0.25 | 0 | 0.18 | 3.84 | 12.48 | 0.43 | 16.93 |
| 2 | 0.5 | 0 | 0.35 | 6.48 | 7.79 | 1.14 | 15.76 |
| 3 | 1 | 0 | 1.20 | 8.84 | 3.75 | 2.60 | 16.39 |
| 4 | 2 | 0 | 1.65 | 9.02 | 1.17 | 3.92 | 15.77 |
| 5 | 3 | 0 | 3.02 | 7.27 | 0.76 | 4.51 | 15.56 |
| 6 | 4 | 0 | 7.85 | 1.06 | 0.69 | 4.61 | 14.22 |
| 7 | 24 | 0 | 8.91 | 0.00 | 0.62 | 4.63 | 14.16 |
| 8 | 0.25 | 2.02 | 10.09 | 0 | 0.74 | 1.85 | 14.69 |
| 9 | 0.5 | 1.53 | 10.85 | 0 | 0.22 | 1.96 | 14.55 |
| 10 | 1 | 0.61 | 10.67 | 0 | 0.07 | 3.26 | 14.61 |
| 11 | 2 | 0.38 | 9.86 | 0 | 0.03 | 4.41 | 14.69 |
| 12 | 3 | 0.36 | 9.35 | 0 | 0.00 | 4.82 | 14.53 |
| 13 | 4 | 0.33 | 9.48 | 0 | 0.00 | 4.90 | 14.71 |
| 14 | 24 | 0.41 | 9.56 | 0 | 0.01 | 4.88 | 14.85 |

*No. 1-7 were those of no treatment of hydrogen peroxide, and No. 8-14 were those after treated by hydrogen peroxide.

The Table 4 shows a concentration of the arsenic compound in the reaction solution. Further, FIG. 10 gives a HPLC-ICP-MS chromatogram (A No. on the graph corresponds to a No. on the table 4). FIG. 11 gives a HPLC-ICP-MS chromatogram (A No. on the graph corresponds to a No. on the table 4). FIG. 12 gives a HPLC-ICP-MS chromatogram (in a case of a treatment of hydrogen peroxide) (A No. on the graph corresponds to a No. on the table 4). FIG. 13 gives a HPLC-ICP-MS chromatogram (A No. on the graph corresponds to a No. 12-14 on the table 4). FIG. 14 shows a variation per hour of the concentration of an arsenic compound in the reaction solution (in a case of a non-treatment of hydrogen peroxide). FIG. 15 shows a variation per hour of the concentration of an arsenic compound in the reaction solution (after hydrogen peroxide treatment). FIG. 16 shows a variation per hour of the percentage of an arsenic compound in the reaction solution (in a case of a non-treatment of hydrogen peroxide). FIG. 17 shows a variation per hour of the percentage of an arsenic compound in the reaction solution (after hydrogen peroxide treatment).

Example 4

The experiment was carried out in the same manner as in Example 3, except that each samples were incubated for 1 hour at 37° C. before the solution A and solution B were added. As shown in the table 5 and FIG. 18, 95% or more of the inorganic arsenic was methylated. The production of tri-methylated arsenic was also confirmed (FIG. 23). A HPLC-ICP-MS chromatogram is shown in FIG. 19. The table 5 shows the concentration of the arsenic compound in the reaction solution.

TABLE 5

| | | Concentration (μmol/L) | | | | | | |
|---|---|---|---|---|---|---|---|---|
| No. | Time (hr) | As (V) | MMA | MMA (III) | As (III) | DMA | TMAO | Total |
| 1 | 0.0 | 0.30 | 7.86 | 0.16 | 15.48 | 1.71 | 0.06 | 25.57 |
| 2 | 1.0 | 0.00 | 14.94 | 1.51 | 1.35 | 5.48 | 0.03 | 23.31 |
| 3 | 24.0 | 0.00 | 9.37 | 6.86 | 1.54 | 6.07 | 0.11 | 23.96 |
| 4 | 24 + $H_2O_2$ | 0.41 | 16.04 | 0.00 | 0.48 | 6.39 | 0.03 | 23.35 |

FIG. 18 shows a variation per hour of the percentage of an arsenic compound in the reaction solution. FIG. 19 gives a HPLC-ICP-MS chromatogram.

Next, the experiment was carried out in the case that various types of reducing agent was used in addition to (or instead of) glutathione (GSH) as a reducing agent. Specifically, in addition to glutathione (GSH) (or instead of GSH), the use of cysteine (Cys), dithiothreitol (DTT) and thioglycol (TG) was examined. Moreover, dimethylsulfoxide (DMSO) was used as solvent for dissolving an artificial vitamin B12 (hydrophobic B12) etc., and used as high boiling point solvent (in order to avoid drying it from evaporation of water in the case that the reaction temperature is 100° C. or more.)

At first, into a 0.1 mL of glass vial tube (attached a silicon seal), GSH (2 mg, 6.5 μmol), 0.5 mg of methyl aquocobyrinic acid heptamethyl ester perchlorate (0.4 μmol), ultrapure water (1 μL) were added (Moreover, vessel attached a silicon seal was used to avoid an evaporation of water. To this was added 1 μL of the inorganic arsenic standard solution (for the atomic absorption, 5 ppm as arsenic), and was put into an oven heated at 130° C. and was reacted for 2 hours. A reaction product was diluted tenfold-thirtyfold with 10% of hydrogen peroxide solution, was analyzed by the HPLC-ICP-MS (Explanation of HB56).

The experiment was carried out in the same manner in the Example, with GSH concentration, Cys concentration, arsenic concentration and temperature be changed as to the other examples in table. The results are shown in table 6-8. The table 6 shows various types of samples No. in the case of the use of various reducing agent, the table 7 shows result of the analysis of various types of samples according to the HPLC-ICP-MS (percentage), and the table 8 shows result of the analysis of various types of samples according to the HPLC-ICP-MS (concentration), respectively.

TABLE 6

| No. | Sample | MeCo (mg) | GSH (mg) | Cys (mg) | DTT (mg) | TG (mg) | DMSO (μL) | H2O (μL) | Total |
|---|---|---|---|---|---|---|---|---|---|
| 1 | HB54 | 1 | 2 | 0.0 | 0.0 | 1.0 | 0.0 | 1.0 | 2.0 |
| 2 | HB55 | 1 | 2 | 0.0 | 0.0 | 1.0 | 1.0 | 1.0 | 3.0 |
| 3 | HB56 | 0.5 | 2 | 0.0 | 0.0 | 1.0 | 0.0 | 1.0 | 2.0 |
| 4 | HB57 | 0.5 | 2 | 0.0 | 0.0 | 0.0 | 1.0 | 1.0 | 2.0 |
| 5 | HB58 | 0.5 | 2 | 0.0 | 0.0 | 0.0 | 1.0 | 1.0 | 2.0 |
| 6 | HB61 | 0.5 | 2 | 0.0 | 0.0 | 0.0 | 1.0 | 1.0 | 2.0 |
| 7 | HB64 | 0.5 | 0 | 2.0 | 0.0 | 0.0 | 1.0 | 1.0 | 6.9 |
| 8 | HB67 | 0.5 | 0 | 2.0 | 0.0 | 0.0 | 1.0 | 1.0 | 4.0 |
| 9 | HB68 | 0.5 | 0 | 2.0 | 0.0 | 0.0 | 1.0 | 1.0 | 18.5 |
| 10 | HB69 | 1 | 0 | 2.0 | 0.0 | 0.0 | 1.0 | 1.0 | 61.3 |
| 11 | HB70 | 1.5 | 0 | 2.0 | 0.0 | 0.0 | 1.0 | 1.0 | 6.3 |
| 12 | HB71 | 0.5 | 0 | 0.0 | 2.0 | 0.0 | 0.0 | 1.0 | #DIV/0 |

MeCo: Methylcobalamin,
GSH: Glutathione (reduced),
Cys: Cysteine,
DTT: Dithiothreitol,
TG: Thioglycolic acid,
DMSO: Dimethylsulfoxide MeCo: methylcobalamin, GSH: glutathione (reducing form), Cys: cysteine, DTT: Dithiothreitol (reducing agent), TG: thioglycol, DMSO: dimethylsulfoxide.

TABLE 7

| | | | | | | | | | (ppm) |
|---|---|---|---|---|---|---|---|---|---|
| No. | Sample | reaction time (h) | reaction tem. (° C.) | As (V) | MMA | DMA | TMAO | TeMA | Total |
| 1 | HB54 | 2 | 130 | 0.154 | 0.000 | 0.072 | 1.103 | 0.281 | 1.610 |
| 2 | HB55 | 2 | 130 | 0.225 | 0.086 | 0.121 | 0.543 | 0.785 | 1.761 |
| 3 | HB56 | 2 | 130 | 0.052 | 0.037 | 0.088 | 0.541 | 0.045 | 0.762 |
| 4 | HB57 | 2 | 130 | 0.077 | 0.035 | 0.067 | 0.233 | 0.034 | 0.446 |
| 5 | HB58 | 2 | 130 | 0.080 | 0.046 | 0.064 | 0.425 | 0.038 | 0.654 |
| 6 | HB61 | 2 | 130 | 0.053 | 0.095 | 0.226 | 0.046 | 0.000 | 0.420 |
| 7 | HB64 | 2 | 130 | 0.037 | 0.022 | 0.072 | 0.527 | 0.046 | 0.703 |
| 8 | HB67 | 2 | 130 | 0.048 | 0.091 | 0.123 | 0.178 | 0.015 | 0.454 |
| 9 | HB68 | 2 | 130 | 0.013 | 0.012 | 0.013 | 0.088 | 0.003 | 0.133 |
| 10 | HB69 | 2 | 130 | 0.006 | 0.006 | 0.010 | 0.121 | 0.016 | 0.158 |
| 11 | HB70 | 2 | 130 | 0.029 | 0.016 | 0.015 | 0.117 | 0.020 | 0.231 |
| 12 | HB71 | 2 | 130 | 0.009 | 0.068 | 0.157 | 0.103 | 0.012 | 0.814 |

TABLE 8

| | | | | | | | | | (%) |
|---|---|---|---|---|---|---|---|---|---|
| No. | Sample | reaction time (h) | reaction tem (° C.) | As (V) | MMA | DMA | TMAO | TeMA | Total |
| 1 | HB54 | 2 | 130 | 9.6 | 0.0 | 4.5 | 68.5 | 17.4 | 100 |
| 2 | HB55 | 2 | 130 | 12.8 | 4.9 | 6.9 | 30.9 | 44.6 | 100 |
| 3 | HB56 | 2 | 130 | 6.8 | 4.9 | 11.5 | 70.9 | 5.9 | 100 |

TABLE 8-continued

| No. | Sample | reaction time (h) | reaction tem (° C.) | As (V) | MMA | DMA | TMAO | TeMA | Total (%) |
|---|---|---|---|---|---|---|---|---|---|
| 4 | HB57 | 2 | 130 | 17.3 | 7.9 | 14.9 | 52.2 | 7.6 | 100 |
| 5 | HB58 | 2 | 130 | 12.3 | 7.1 | 9.8 | 65.0 | 5.8 | 100 |
| 6 | HB61 | 2 | 130 | 12.7 | 22.5 | 53.7 | 11.0 | 0.0 | 100 |
| 7 | HB64 | 2 | 130 | 5.2 | 3.2 | 10.2 | 74.9 | 6.5 | 100 |
| 8 | HB67 | 2 | 130 | 10.6 | 19.9 | 27.0 | 39.2 | 3.3 | 100 |
| 9 | HB68 | 2 | 130 | 10.1 | 8.8 | 9.7 | 65.9 | 2.6 | 100 |
| 10 | HB69 | 2 | 130 | 3.6 | 3.6 | 6.1 | 76.8 | 9.9 | 100 |
| 11 | HB70 | 2 | 130 | 12.5 | 7.1 | 6.3 | 50.8 | 8.6 | 100 |
| 12 | HB71 | 2 | 130 | 1.0 | 8.4 | 19.3 | 12.6 | 1.4 | 100 |

Further, FIG. 20 gives a HPLC-ICP-MS chromatogram (corresponding to a No. 10 of the table 6, a No. 10 of the table 7 and a No. 10 of the table 8). As shown in the HPLC-ICP-MS of FIG. 20, trimethyl arsine oxide having a low toxicity was obtained as a principal product in the reaction mixture (77%).

Examples 5-10

Next, various types of methyl aquocobyrinic acid derivative were made, and the effect of the various types of methyl aquocobyrinic acid derivative was examined. Hereinafter, the examples 5-10 of the present invention will be explained.

Synthesis of methyl aquocobyrinic acid sodium perchlorate [$(CH_3)(H_2O)Cob(III)7COONa]ClO_4$, from methyl aquocobyrinic acid heptamethyl ester perchlorate [$(CH_3)(H_2O)Cob(III)7C_1ester]ClO_4$.

[Chemical 11]

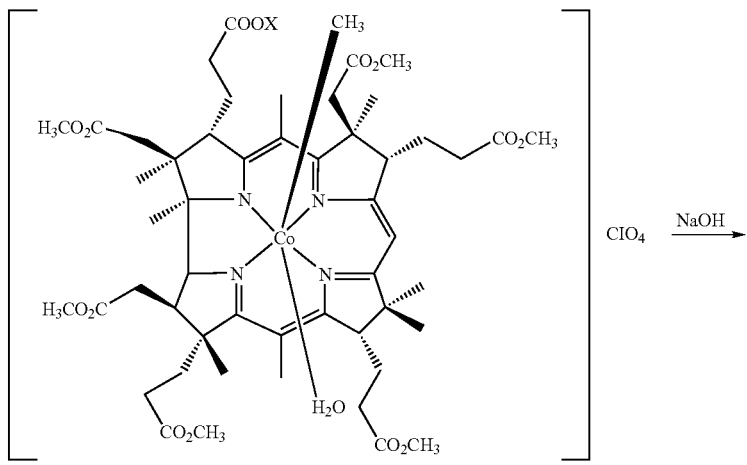

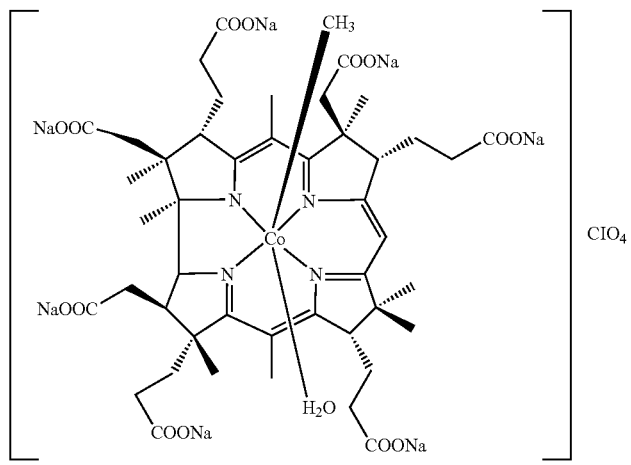

The above [Chemical 11] shows a reaction from methyl aquocobyrinic acid heptamethyl ester perchlorate [(CH$_3$)(H$_2$O)Cob(III)7C$_1$ester]ClO$_4$ to methyl aquocobyrinic acid sodium perchlorate [(CH$_3$)(H$_2$O)Cob(III)7COONa]ClO$_4$.

Six glass vials pre-washed with 5% of nitric acid were prepared. To this was measured off 5 mg (4.3 μmol) of hydrophobic vitamin B$_{12}$. To this was added 10 μL of methanol, and was stirred, and then the hydrophobic vitamin B$_{12}$ was dissolved in methanol. To this was added 20 μL of 4 mol/L sodium hydroxide aqueous solution, and was stirred, and was reacted in a temperature-controlled bath maintained at 30° C. in predetermined time. The reaction time was 1 hour (solution A-1, solution B-1), 4 hours (solution A-2, solution B-2), 20 hours (solution A-3, solution B-3).

The confirmation of a methyl aquocobyrinic acid derivative actually obtained was carried out as follows:

FIG. 21 gives an electronic spectrum of methyl aquocobyrinic acid heptamethyl ester perchlorate [(CH$_3$)(H$_2$O)Cob(III)7C$_1$ester]ClO$_4$. A shows those before exposure to light, and B shows those after exposure to light, respectively. FIG. 22 gives an electronic spectrum of methyl aquocobyrinic acid sodium perchlorate [(CH$_3$)(H$_2$O)Cob(III)COONa]ClO$_4$. In the FIG. 22, A shows those before exposure to light, and B shows those after exposure to light, respectively.

As shown in FIG. 21, in those before exposure to light, it shown an absorption spectrum of a methylated cobalt complex (A). In those after exposure to light, it shown a spectrum of a cobalt complex wherein a methyl group was cleaved (B). On the other hand, as shown in FIG. 22, in those before exposure to light, it shown an absorption spectrum of a methylated cobalt complex (A), even if it was a complex after an alkali hydrolysis reaction. It was confirmed that a Co—CH$_3$ bond was maintained after an alkali hydrolysis reaction because in those after exposure to light, it shown a spectrum of a cobalt complex wherein a methyl group was cleaved (B). The confirmation of the resolvability of methyl aquocobyrinic acid sodium perchlorate to water after an alkali hydrolysis reaction was carried out as follows: The solvent was eliminated by a freeze-drying method from the solution A-3, the solution was dried. To this was added 50 μL of a ultrapure water and was stirred. No precipitate occurred. On the other hand, although 5 mg of a hydrophobic vitamin B$_{12}$ {methyl aquocobyrinic acid heptamethyl ester perchlorate [(CH$_3$)(H$_2$O)Cob(III)7C$_1$ester]ClO$_4$} and 50 μL of a ultrapure water were added and stirred, it was not completely dissolved. In a view of the above-mentioned results, it is clear that a methyl ester of a hydrophobic vitamin B$_{12}$ {methyl aquocobyrinic acid heptamethyl ester perchlorate [(CH$_3$)(H$_2$O)Cob(III)7C$_1$ester]ClO$_4$} was cleaved by alkali hydrolysis reaction, and a water-soluble methyl aquocobyrinic acid sodium perchlorate [(CH$_3$)(H$_2$O)Cob(III)COONa]ClO$_4$ was formed. Further, it was confirmed by an electronic spectrum after exposure to light that a Co—CH$_3$ bond which is needed for the methylation was maintained.

A $^1$H-NMR of methyl aquocobyrinic acid heptamethyl ester perchlorate [(CH$_3$)(H$_2$O)Cob(III)7C$_1$ester]ClO$_4$ is shown in FIG. 24. An Identification of a $^1$H-NMR as to a methyl group of [(CH$_3$)(H$_2$O)Cob(III)7C$_1$ester]ClO$_4$ is shown in No. 1-9 of the figure (FIG. 24). A CH$_3$ signal directly bonded to Co atom comes in at −0.15 ppm. A proton of seven methyl ester of [(CH$_3$)(H$_2$O)Cob(III)7C$_1$ester]ClO$_4$ comes in as seven signal between at 3.5 ppm and at 3.8 ppm. A $^1$H-NMR signal after methyl aquocobyrinic acid heptamethyl ester perchlorate [(CH$_3$)(H$_2$O)Cob(III)7C$_1$ester]ClO$_4$ is hydrolyzed, is shown in FIG. 25. It is clear that seven methyl ester groups was hydrolyzed because the proton signal of seven methyl ester groups of [(CH$_3$)(H$_2$O)Cob(III)7C$_1$ester]ClO$_4$ were disappeared in FIG. 25 which seven signals were came in between at 3.5 ppm and 3.8 ppm in FIG. 24, respectively. Further, it can be recognized that no cleavage of a Co—C bond is occurred by the alkali hydrolysis because the signal derived from methyl group directly bonded to Co atom is confirmed. In a view of the above, a conformation of [(CH$_3$)(H$_2$O)Cob(III)7COONa]ClO$_4$ (methyl aquocobyrinic acid sodium perchlorate) can be confirmed.

<Preparation of an Arsenic Methylated Reaction Solution>

The solution A-1, A-2 and A-3 were neutralized by using 6 mol/L of hydrochloric acid aqueous solution and 0.01 mol/L-1 mol/L of sodium hydroxide solution so as not to exceed beyond 50 μL as a total volume. To the solution B-1, B-2 and B-3 were added 20 μL of the ultrapure water. 20 mg (65 μmol) of a reduced glutathione (GSH) was added to a vessel and was stirred. To this was added 2 μL (2.7 nmol as arsenic trioxide) of arsenic trioxide solution which is trivalent inorganic arsenic (a standard solution for the atomic absorption, 100 ppm). As to the concentration of the reaction solution are as follows: glutathione (reduced form) (GSH): 1.3 mmol/L, hydrolysis substance of hydrophobic vitamin B12 (WSHB): 0.086 mmol/L, trivalent inorganic arsenic: 5 nmol/L. A preparation condition of the reaction agent is shown in the table 9. This was charged into a hemathermal heater, was reacted at a given temperature for predetermined time. Reaction conditions are shown in the table 10.

<Analysis>

After the reaction was terminated, the reaction solution was treated by 10% of hydrogen peroxide solution, and was diluted 500 folds by the ultrapure water, and the qualitative and quantitative analysis thereof was carried out by using the HPLC-ICP-MS method. 5 types of chemical species, namely, pentavalent arsenic, pentavalent monomethyl arsenic (MMA), pentavalent dimethyl arsenic (DMA), pentavalent trimethyl arsenic (TMAO), and tetramethyl arsenic (TeMA) were prepared, an analytical curve was made by a standard sample, and a quantitative determination was carried out. The relative concentration after the reaction was calculated by the below defined formula.

The relative concentration of $i$As(V)=100%×[$i$As(V)/($i$As(V)+MMA+DMA+TMAO+TeMA)]

The relative concentration of MMA=100%×[MMA/($i$As(V)+MMA+DMA+TMAO+TeMA)]

The relative concentration of DMA=100%×[DMA/($i$As(V)+MMA+DMA+TMAO+TeMA)]

The relative concentration of TMAO=100%×[TMAO/($i$As(V)+MMA+DMA+TMAO+TeMA)]

The relative concentration of TeMA=100%×[TeMA/($i$As(V)+MMA+DMA+TMAO+TeMA)]

Further, a recovery percentage of arsenic was calculated by the below formula.

The recovery percentage=100%×(arsenic concentration before the reaction/arsenic concentration after the reaction)=100%×[$i$As($III$)/($i$As(V)+MMA+DMA+TMAO+TeMA)]

The result of the example 5 (A-1), example 6 (A-2), example 7 (A-3), example 8 (B-1), example 9 (B-2), example 10 (B-3) are shown in the table 11. The table 9 shows the hydrolysis conditions of hydrophobic vitamin B12. The table 10 shows the reaction conditions. The table 11 shows the yield (relative yield, absolute yield) and the recovery percentage.

TABLE 9

| | Hydrolysis conditions | | | | Neutralization conditions | | | |
| --- | --- | --- | --- | --- | --- | --- | --- | --- |
| | methylation agent | solvent | NaOH | | HCl | NaOH | | after |
| No. | Co (mg) | MeOH (μL) | 4N (μL) | Hydrolysis (hr) | 6N (μL) | 1N (μL) | 0.1 (μL) | 0.01N (μL) | neutralization pH |
| A-1 | 5 | 10 | 20 | 1 | 12 | 2 | 6 | — | 4~5 |
| A-2 | 5 | 10 | 20 | 4 | 12 | — | 8 | — | 4~5 |
| A-3 | 5 | 10 | 20 | 20 | 10 | — | — | 10 | 5~6 |
| B-1 | 5 | 10 | 20 | 1 | — | — | — | — | — |
| B-2 | 5 | 10 | 20 | 4 | — | — | — | — | — |
| B-3 | 5 | 10 | 20 | 20 | — | — | — | — | — |

TABLE 10

| | Preparation conditions | | | | | |
| --- | --- | --- | --- | --- | --- | --- |
| | Solvent | reducing agent | arsenic iAs (III) | before reaction | reaction conditions | |
| No. | H2O (μL) | GSH (mg) | (100 ppm) (μL) | iAs3 (ppm) | Temp. (° C.) | Time (hr) |
| A-1 | — | 20 | 2 | 4 | 100 | 2 |
| A-2 | — | 20 | 2 | 4 | 100 | 2 |
| A-3 | — | 20 | 2 | 4 | 100 | 2 |
| B-1 | 20 | 20 | 2 | 4 | 100 | 2 |
| B-2 | 20 | 20 | 2 | 4 | 100 | 2 |
| B-3 | 20 | 20 | 2 | 4 | 100 | 2 |

TABLE 11

| | Result of analysis | | | | | | |
| --- | --- | --- | --- | --- | --- | --- | --- |
| | Products (Yield) | | | | | | Recovery percentage (%) |
| No. | iAs5 (ppm) | MMA (ppm) | DMA (ppm) | TMA (ppm) | TeMA (ppm) | Total (ppm) | |
| A-1 | 0.0 | 0.0 | 0.0 | 2.8 | 1.3 | 4.0 | 101 |
| A-2 | 0.0 | 0.0 | 0.0 | 3.6 | 0.3 | 3.9 | 97 |
| A-3 | 0.0 | 0.0 | 0.0 | 3.9 | 0.3 | 4.1 | 103 |
| B-1 | 0.0 | 0.0 | 0.0 | 3.6 | 0.2 | 3.8 | 95 |
| B-2 | 0.0 | 0.0 | 0.0 | 3.8 | 0.2 | 4.0 | 101 |
| B-3 | 0.0 | 0.0 | 0.0 | 3.9 | 0.1 | 4.0 | 99 |
| No. | iAs5 (%) | MMA (%) | DMA (%) | TMA (%) | TeMA (%) | Total (%) | |
| | Relative rate | | | | | | |
| A-1 | 0 | 0 | 0 | 69 | 31 | 100 | |
| A-2 | 0 | 0 | 0 | 92 | 8 | 100 | |
| A-3 | 0 | 0 | 0 | 94 | 6 | 100 | |
| B-1 | 0 | 0 | 0 | 94 | 6 | 100 | |
| B-2 | 0 | 0 | 0 | 95 | 5 | 100 | |
| B-3 | 0 | 0 | 0 | 99 | 1 | 100 | |
| | Absolute yield | | | | | | |
| A-1 | 0 | 0 | 0 | 69 | 32 | 101 | |
| A-2 | 0 | 0 | 0 | 90 | 7 | 97 | |
| A-3 | 0 | 0 | 0 | 97 | 7 | 103 | |
| B-1 | 0 | 0 | 0 | 89 | 6 | 95 | |
| B-2 | 0 | 0 | 0 | 96 | 5 | 101 | |
| B-3 | 0 | 0 | 0 | 98 | 1 | 99 | |

As shown in the Examples 5-10, arsenic trioxide was selectively converted to trimethyl arsenic (TMAO) having a low toxicity. In particular, in the Examples 6-10, 90% or more of the relative rate of TMAO was obtained. Further, it was revealed that a conversion to water-soluble cobyrinic acid by hydrolysis treatment of methyl ester group of hydrophobic vitamin B12 (cobyrinic acid heptamethyl ester) makes it possible to improve an efficiency of the detoxified treatment according to the methylation reaction of toxic arsenic trioxide in aqueous solution.

On the other hand, in the case of hydrophobic vitamin B12, (X=$CH_3$) in [Chemical 1], as a beneficial effect on compound, it was revealed that it has effects that (1) it is easy to extract it with an organic solvent from the reaction mixture solution, and it was recyclable, (2) a reactivity in an aqueous solutions system mixed with the organic solvent is equal or more compared with that of the water-soluble vitamin B12 (methylcobalamin).

INDUSTRIAL APPLICABILITY

The composition of the present invention makes it possible to produce a method of detoxifying the harmful compound containing arsenic etc., more practically and industrially. The present inventions make a significant contribution in the broad fields of treatments of the industrial waste etc., and environmental protections concerning a polluted mud or a soil, since the harmless compound obtained by converting the harmful compound containing arsenic etc., to more harmless compound by the alkylation, is extremely stable and safe.

The invention claimed is:
1. A composition for alkylation, comprising:
an organic metal complex having a cobalt-carbon bond, the organic metal complex being a methyl aquocobyrinic acid derivative as shown in the general formula [Chemical 13]:

[Chemical 13]

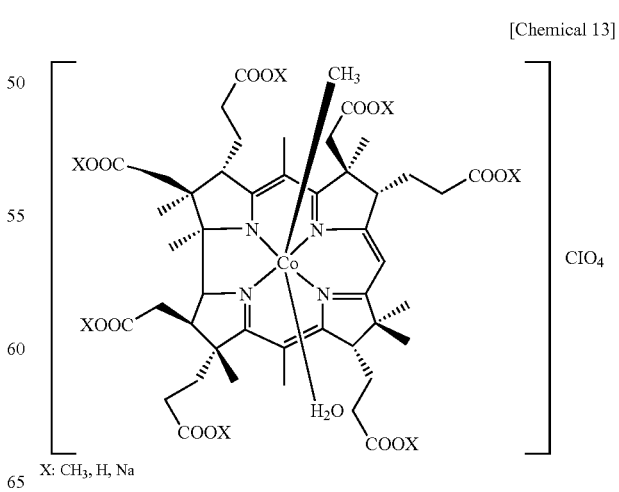

X: $CH_3$, H, Na where X is CH₃, H or Na; and, a reducing agent capable of reducing at least one metal selected from the group consisting of arsenic, antimony and selenium in the presence of the organic metal complex.

2. A composition for alkylation according to claim 1, wherein the reducing agent is a compound having a SH group.

3. A composition for alkylation according to claim 2, wherein the compound having a SH group is at least one selected from the group consisting of glutathione, reduced glutathione (GSH), cysteine, S-adenosyl cysteine, dithiothreitol and thioglycol.

* * * * *